(12) United States Patent
Hoeferl-Prantz et al.

(10) Patent No.: US 9,346,853 B2
(45) Date of Patent: May 24, 2016

(54) SYNTHESIS OF TELAPREVIR AND BOCEPREVIR, OR PHARMACEUTICALLY ACCEPTABLE SALTS OR SOLVATES AS WELL AS INTERMEDIATE PRODUCTS THEREOF INCLUDING β-AMINO ACIDS PREPARED VIA MUKAIYAMA ALDOL ADDITION

(71) Applicant: Sandoz AG, Basel (CH)

(72) Inventors: Kathrin Hoeferl-Prantz, Kundl (AT); Wolfgang Felzmann, Kundl (AT); Thorsten Wilhelm, Kundl (AT); David Benito-Garagorri, Kundl (AT)

(73) Assignee: Sandoz AG, Basel (CH)

( * ) Notice: Subject to any disclaimer, the term of this patent is extended or adjusted under 35 U.S.C. 154(b) by 0 days.

(21) Appl. No.: 14/408,465

(22) PCT Filed: Jun. 19, 2013

(86) PCT No.: PCT/EP2013/062737
§ 371 (c)(1),
(2) Date: Dec. 16, 2014

(87) PCT Pub. No.: WO2013/189980
PCT Pub. Date: Dec. 27, 2013

(65) Prior Publication Data
US 2015/0183824 A1    Jul. 2, 2015

(30) Foreign Application Priority Data

Jun. 20, 2012  (EP) .................................... 12172775

(51) Int. Cl.
| | | |
|---|---|---|
| *A61K 38/04* | (2006.01) | |
| *C07K 5/00* | (2006.01) | |
| *C07K 7/00* | (2006.01) | |
| *C07K 16/00* | (2006.01) | |
| *C07K 17/00* | (2006.01) | |
| *C07K 5/107* | (2006.01) | |
| *C07D 403/12* | (2006.01) | |
| *C07K 5/087* | (2006.01) | |
| *C07K 5/083* | (2006.01) | |
| *C07K 5/062* | (2006.01) | |
| *C07C 227/02* | (2006.01) | |
| *C07C 231/02* | (2006.01) | |
| *C07C 231/12* | (2006.01) | |
| *C07C 237/06* | (2006.01) | |
| *C07F 7/18* | (2006.01) | |
| *C07K 1/10* | (2006.01) | |
| *A61K 38/00* | (2006.01) | |

(52) U.S. Cl.
CPC .............. *C07K 5/1016* (2013.01); *C07C 227/02* (2013.01); *C07C 231/02* (2013.01); *C07C 231/12* (2013.01); *C07C 237/06* (2013.01); *C07D 403/12* (2013.01); *C07F 7/1872* (2013.01); *C07K 1/10* (2013.01); *C07K 5/06034* (2013.01); *C07K 5/0808* (2013.01); *C07K 5/0812* (2013.01); *A61K 38/00* (2013.01)

(58) Field of Classification Search
CPC ... A61K 31/7056; A61K 38/00; A61K 38/06; C07K 5/0808; C07K 5/0812
See application file for complete search history.

(56) References Cited

FOREIGN PATENT DOCUMENTS

| | | |
|---|---|---|
| WO | WO 2004/113294 A1 | 12/2004 |
| WO | WO 2007/022459 A2 | 2/2007 |
| WO | WO 2007/109023 A1 | 9/2007 |
| WO | WO 2007/138928 A1 | 12/2007 |
| WO | WO 2009/114633 A1 | 9/2009 |
| WO | WO 2009/152474 A2 | 12/2009 |

OTHER PUBLICATIONS

Gizecki et al., Diastereoselective preparation of novel tetrahydrooxazinones via heterocycloaddition of N-Boc, O-Me-acetals. Tetrahedron Letters. 2004;45(52):9589-92.
Greene's Protective Groups in Organic Synthesis, 4$^{th}$ Edition. John Wiley & Sons. 2007:189-96, 102-20, 553-61, 725-35, 748-56, 814-8.
Han et al., Recent development of peptide coupling reagents in organic synthesis. Tetrahedron. 2004;60(11):2447-67.
Hattori et al., Highly selective and operationally simple synthesis of enantiomerically pure .beta.-amino esters via double stereodifferentiation. JACS. 1993;115(3):1151-2.
Hattori et al., Practical preparation of α-hydroxy-β-amino ester units; Stereoselective synthesis of taxol side chain and norstatine. Tetrahedron. 1994;50(9):2785-92.
Khim et al., Solid and solution phase synthesis of α-keto amides via azetidinone ring-opening: Application to the synthesis of poststatin. Tetrahedron Letters. 1999; 40(10):1827-30.
Kobayashi et al., Catalytic Asymmetric Synthesis of Both Syn- and Anti-β-Amino Alcohols. JACS. 1998;120:431-2.
March's Advanced Organic Chemistry: Reactions, Mechanisms, and Structure. John Wiley & Sons. 2007:1185-7.
Pelotier et al., The Formation of Silylated β-Lactams from Silylketenes through Lewis Acid Promoted [2+2] Cycloaddition: A Combined Theoretical and Experimental Study. Eur J Org Chem. 2005;2005(12):2599-606.
Yin et al., Recent Applications of α-Amino Sulfones as in situ Equivalents of Activated Imines for Asymmetric Catalytic Nucleophilic Addition Reactions. Syntheses 2010;(21):3583-95.

*Primary Examiner* — James H Alstrum Acevedo
*Assistant Examiner* — Kaipeen Yang
(74) *Attorney, Agent, or Firm* — Wolf, Greenfield & Sacks, P.C.

(57) ABSTRACT

The invention relates to synthetic routes for preparing telaprevir and boceprevir, and its intermediates as well as peptides other than telaprevir. The synthetic routes are based on a Mukaiyama aldol addition reaction of a silyl enol ether or an enolate with an imine. The invention also refers to novel intermediates for preparing telaprevir/boceprevir or other peptides.

3 Claims, 3 Drawing Sheets

Figure 1 – Yamamoto.
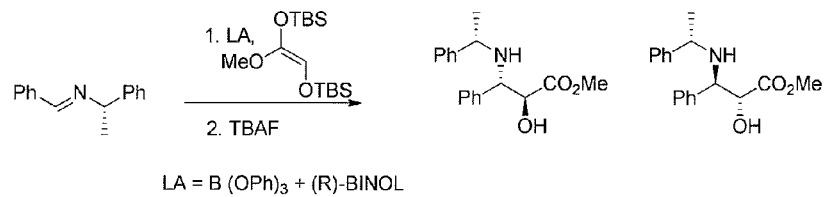
LA = B (OPh)₃ + (R)-BINOL
Figure 2
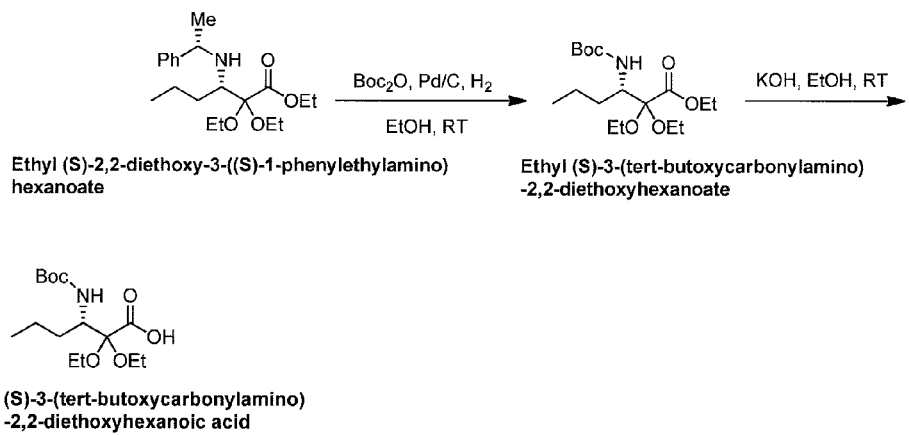
Ethyl (S)-2,2-diethoxy-3-((S)-1-phenylethylamino)
hexanoate
Ethyl (S)-3-(tert-butoxycarbonylamino)
-2,2-diethoxyhexanoate
(S)-3-(tert-butoxycarbonylamino)
-2,2-diethoxyhexanoic acid
Figure 3
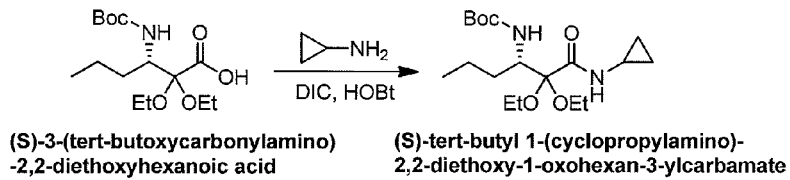
(S)-3-(tert-butoxycarbonylamino)
-2,2-diethoxyhexanoic acid
(S)-tert-butyl 1-(cyclopropylamino)-
2,2-diethoxy-1-oxohexan-3-ylcarbamate (S)-tert-butyl 1-(cyclopropylamino)-
2,2-diethoxy-1-oxohexan-3-ylcarbamate (3S)-3-Amino-N-cyclopropyl-
2,2-diethoxyhexanamide

SYNTHESIS OF TELAPREVIR AND BOCEPREVIR, OR PHARMACEUTICALLY ACCEPTABLE SALTS OR SOLVATES AS WELL AS INTERMEDIATE PRODUCTS THEREOF INCLUDING β-AMINO ACIDS PREPARED VIA MUKAIYAMA ALDOL ADDITION

RELATED APPLICATIONS

This application is a national stage filing under 35 U.S.C. §371 of International Application PCT/EP2013/062737 entitled "SYNTHESIS OF TELAPREVIR AND BOCEPREVIR, OR PHARMACEUTICALLY ACCEPTABLE SALTS OR SOLVATES AS WELL AS INTERMEDIATE PRODUCTS THEREOF INCLUDING β-AMINO ACIDS PREPARED VIA MUKAIYAMA ALDOL ADDITION," filed Jun. 19, 2013, which claims priority to EP Application No. EP 12172775.4, filed Jun. 20, 2012. The entire disclosure of each of the prior applications is incorporated by reference herein in its entirety.

The invention relates to four alternative synthetic routes for preparing β-amino acids, usable in the synthesis of telaprevir and boceprevir and/or intermediates thereof, but not being restricted to it. The synthetic routes are based on a Mukaiyama aldol addition reaction of a silyl enol ether or an enolate with an imine. The invention also refers to novel intermediates for preparing telaprevir or other peptides.

BACKGROUND PRIOR ART

Telaprevir/boceprevir is a protease inhibitor that can be used as antiviral drug. By way of example, telaprevir inhibits the hepatitis C virus NS3-4A serine protease.

Although some processes for the synthesis of telaprevir/boceprevir and its pharmaceutically acceptable salts are available, it is an object of the present invention to provide alternative processes, in particular enhanced processes that overcome at least one of the problems of the prior art processes.

WO 2007/138928 A1 discloses the preparation of a compound having the following formula:

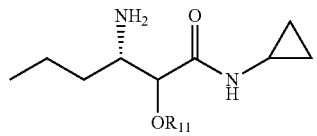

15a (R11=H) by using optically active oxazolines as intermediates.

WO 2007/109023 A1 describes the preparation of the same compound via epoxidation of an α,β-unsaturated carboxyamide, azidation of the epoxide, reduction of the azide group to provide an amine and subsequent racemic resolution.

WO 2009/114633 A1 also describes a synthesis for the above compound starting from norvaline. In order to elongate the chain of norvaline, a cyanide addition is performed.

WO2009/152474 A2 describes a process for the preparation of 3-amino-N-cyclopropyl-2-hydroxyalkane amide derivatives as key intermediates in the production of HCV inhibitors. The synthesis route comprises a step of reacting an aminoaldehyde with a cyclopropyl isocyanide to obtain an 3-amino-2-hydroxycarboxylic acid amide.

Yamamoto (Journal of the American Chemical Society 1993, 115, 1151 and Tetrahedron 1994, 50, 9, 2785) describes a process for the synthesis of building blocks for the synthesis of taxol. The synthesis includes the use of an imine, a silyl enol ether, a Lewis acid (LA) and chiral boron reagents (see FIG. 1).

SUMMARY OF THE INVENTION

Some of the known processes for the preparation of telaprevir are based on the use of 3-amino-N-cyclopropyl-2-hydroxyhexanamide as intermediate. The processes described herein are based on the preparation of 3-amino-N-cyclopropyl-2,2-dialkoxyhexanamides and 3-amino-N-cyclopropyl-2-hydroxyhexanamides. These intermediates are accessible via Mukaiyama aldol addition reaction of a silyl enol ether (e.g. a compound of Formula 3 below) or an enolate (e.g. obtained from a compound of Formula 11a in the presence of a strong base) with an imine or an in situ generated imine. The intermediates can be reacted with an acid moiety such as

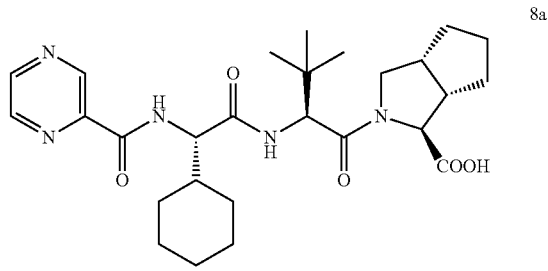 [SMILES: CC(C)(C)[C@H](NC(=O)[C@@H](NC(=O)c1cnccn1)C1CCCCC1)C(=O)N1C[C@@H]2CCC[C@@H]2[C@H]1C(=O)O]

8a in order to provide monohydroxy or dialkoxy ketal intermediates of telaprevir/boceprevir which can be easily converted into telaprevir/boceprevir.

It has also been unexpectedly found that the reaction sequences described herein are useful for the preparation of various compounds other than those required for the telaprevir/boceprevir synthesis. In particular, the invention can be used for preparing various derivatives such as 3-amino-hexanamide derivatives which can then be coupled with acid compounds other than the compound of Formula 8a, which is used for the synthesis of telaprevir, via peptide bonding.

It has also been found that the Mukaiyama aldol addition with silyl enol ethers described herein can be used for the stereoselective preparation of 3-amino-N-cyclopropyl-2,2-dialkoxyhexanamides and 3-amino-N-cyclopropyl-2-hydroxyhexanamides, wherein the stereo information is provided by a chiral group of the imine component. Said stereo information cannot be lost during the further steps of the telaprevir synthesis. The stereo information required for the telaprevir synthesis can be provided by (S)-phenylethylamine which is readily available and cheap. The same advantages can be achieved when preparing compounds other than telaprevir via peptide coupling.

In particular, it has been found that the combination of imine 2a and silyl enol ethers 3 according to the present invention has a high reactivity and allows achieving high selectivities even without using chiral lewis acids.

Furthermore, the oxidation state in the α-position of the enol component used in the Mukaiyama aldol addition can freely be chosen independent of the imine. For example, after coupling 3-amino-N-cyclopropyl-2,2-dialkoxyhexanamides with the acid component 8a, the obtained telaprevir acetal intermediate already has the oxidation state of telaprevir and the acetal can thus easily be converted to telaprevir/boceprevir. This may provide a synthetic route with a reduced number of process steps.

Thus, the final chemical transformation of diethoxy-telaprevir toward telaprevir is an acid deprotection of an acetal, as opposed to the prior art route in which the last step is an oxidation of an alcohol to a ketone. Oxidative transformations on substrates containing oxidation-sensitive functional groups such as heteroaromatic systems, ketones and α-ketoamides are well known to give rise to byproducts: All these moieties are present in telaprevir and therefore the formation of oxidative byproducts is very likely and has been proven in our laboratory experimentally. By using the route described herein with no oxidation as final step, the formation of these byproducts is avoided. Thus, the route of the present invention using diethoxy-telaprevir as final intermediate secures the absence of these oxidative byproducts. Given the fact that telaprevir prepared according to the prior art route (in which the last step is an oxidation of an alcohol to a ketone) contains these byproducts, an improvement of the product's quality can be achieved by using the oxidation free route described herein, without additional purification measures being necessary. Also one of this impurities (IMP1) can be removed via additional basic extraction at pH>11 (which can cause epimerization) (see Example 27), the other one is found in commercially available products.

If 3-amino-N-cyclopropyl-2-hydroxyhexanamides are used for the telaprevir synthesis, the obtained telaprevir precursor is a protected α-hydroxy compound which can be oxidized to provide telaprevir.

Thus, the invention relates to processes for the preparation of telaprevir/boceprevir as defined in the claims. Furthermore, it relates to the preparation of intermediates as defined in the claims as well as to the intermediates themselves.

DESCRIPTION OF FIGURES

FIG. 1: Shows a process developed by Yamamoto et al. (see above citation) for the synthesis of building blocks for the synthesis of taxol. The synthesis includes the use of an imine, a silyl enol ether, a lewis acid (LA) and chiral boron reagents. TBAF=tetra-n-butylammonium fluoride, (R)-BINOL=(R)-(+)-1,1'-Bi(2-naphthol).

FIG. 2: Shows the preparation of (S)-3-(tert-butoxycarbonylamino)-2,2-diethoxyhexanoic acid by protecting group exchange of Ethyl(S)-2,2-diethoxy-3-((S)-1-phenylethylamino) hexanoate and saponification of Ethyl(S)-3-(tert-butoxycarbonylamino)-2,2-diethoxyhexanoate.

FIG. 3: Shows the preparation of (S)-tert-butyl 1-(cyclopropylamino)-2,2-diethoxy-1-oxohexan-3-ylcarbamate by amidation of (S)-3-(tert-butoxycarbonylamino)-2,2-diethoxyhexanoic acid.

DETAILED DESCRIPTION

Figure 4:
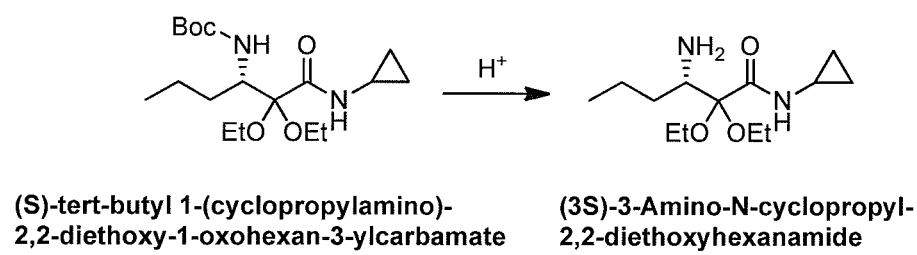
FIG. 4: Shows the preparation of (3S)-3-Amino-N-cyclopropyl-2,2-diethoxyhexanamide by deprotection of (S)-tert-butyl 1-(cyclopropylamino)-2,2-diethoxy-1-oxohexan-3-ylcarbamate.

The invention generally relates to processes for the preparation of telaprevir according to Formula 1

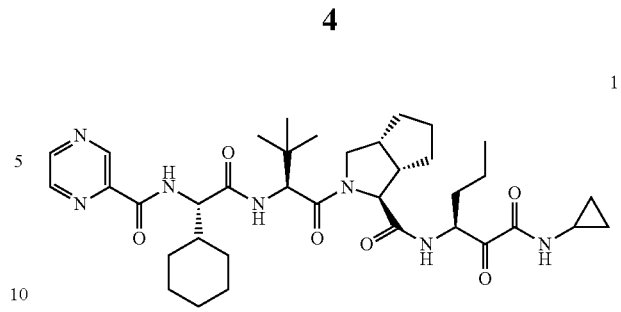

1 and boceprevir according to Formula 25

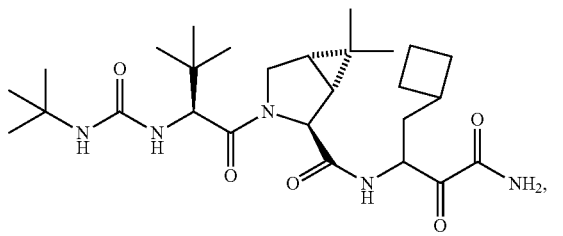

25 or a pharmaceutically acceptable salt or solvate as well as intermediates thereof.

Pharmaceutically acceptable salts include, but are not limited to the group consisting of hydrochloride, hydrobromide, sulphates or phosphates as well as organic salts such as acetate, citrate, maleate, succinate, lactate, and benzoate. Pharmaceutically acceptable salts can be obtained according to standard methods, for example by addition of the respective acid to telaprevir or boceprevir as free base.

The invention can also be used to form peptides other than telaprevir/boceprevir for example the compounds according to the Formulas 9/9' and 16:

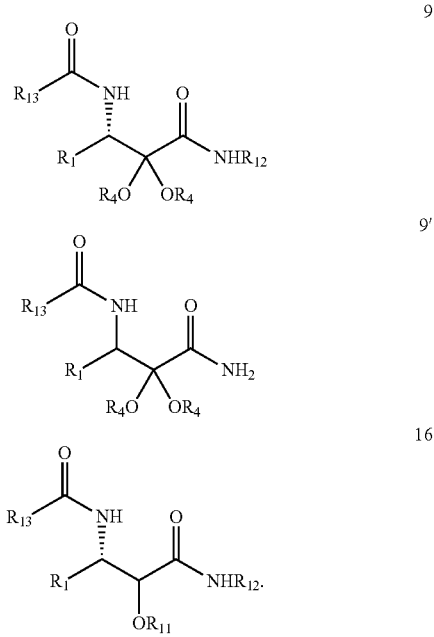

In the context of this invention, the term "Lewis acid" has the meaning which is well-known in the art and can be defined as a molecular entity that is an electron-pair acceptor and therefore able to react with a Lewis base to form a Lewis adduct by sharing the electron pair furnished by the Lewis base. Thus, examples of Lewis acids include, but are not limited to, proton (H+), boron trifluoride and its diethyl ether adduct, tetrafluoroboric acid and its diethyl ether adduct, magnesium dibromide and its diethyl ether adduct, aluminium trichloride or anhydrous iron trichloride.

In a first step of the processes described herein, an imine compound of Formula 2

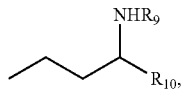

2 or a compound of Formula 10a

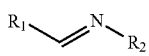

10a which generates an imine in situ, is reacted with an silyl enol ether or an enolate.

The silyl enol ether or enolate can be selected/derived from the following group of compounds:

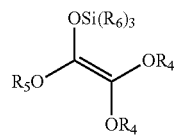

3

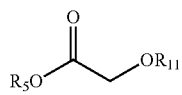

17a

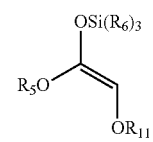

12a

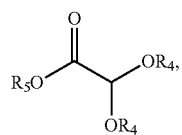

11a wherein the compounds of Formula 17a and 11a can be converted to an enolate in situ by use of a strong base such as lithiumdiisopropylamide.

According to a first aspect, the compounds of Formula 2/2a and 3

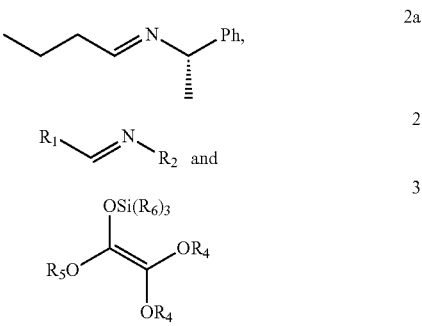

are used as starting materials, wherein the compound of Formula 2a corresponds to the compound of Formula 2 with $R_1$=n-propyl and $R_2$=(S)—CH(CH$_3$)Ph and in the compound of Formula 3 $R_4$, $R_5$ and $R_6$ are preferably independently methyl or ethyl.

The below definitions for groups $R_1$-$R_{13}$ can be applied in the context of the first aspect:

$R_1$ is selected from the group consisting of linear, branched, or cyclic aliphatic groups, aromatic groups, and heteroaromatic groups as well as combinations thereof, preferably in all aforementioned definitions $R_1$ has 1-12 carbon atoms or 1-6 carbon atoms, in particular $R_1$ is a linear, branched, or cyclic aliphatic $C_1$-$C_{12}$ or $C_1$-$C_6$ group, in addition in all aforementioned definitions $R_1$ is preferably a saturated and unsubstituted hydrocarbon group, i.e. a group that only comprises hydrogen and carbon atoms; preferably $R_1$ is a propyl group;

$R_2$ is selected from the group consisting of linear or branched arylalkyl groups, aromatic groups, carbamates and heteroaromatic groups as well as combinations thereof; preferably in all aforementioned definitions $R_2$ has 1-12 carbon atoms or 1-6 carbon atoms, in particular $R_2$ is an arylalkyl group, preferably a methylene aromatic group, preferably a benzylic, $C_7$-$C_{12}$ group, in addition in all aforementioned definitions $R_2$ preferably only comprises hydrogen and carbon atoms; preferably $R_2$ is CH(CH$_3$)Ph, preferably $R_2$ is CH(CH$_3$)Ph with (S)-configuration; Preferably, $R_2$ has one or more stereocenters, preferably the stereocenter is in α-position to the imine-N atom.

In order to provide a stereoselective reaction of the compound of Formula 2, e.g. 2a, with the compound of Formula 3, $R_2$ in the compound of Formula 2 has to have one stereogenic center, preferably in α-position to the imine-N atom, with one stereoconfiguration being present in excess. Generally, stereocentres in α-position to the imine-N atom will lead to a large of excess (such as e.g. more than 5:1) of the preferred diastereomer (as indicated by the newly formed stereogenic centre in the compounds of Formula 4/4a and compounds prepared from these compounds). If no such stereogenic center is present in α-position to the imine-N atom, the reaction will not provide a large excess of a preferred diastereomer.

$R_4$ is selected from the group consisting of linear, branched, or cyclic aliphatic groups, aromatic groups, and heteroaromatic groups as well as combinations thereof, preferably in all aforementioned definitions $R_4$ has 1-12 carbon atoms or 1-6 carbon atoms, in particular $R_4$ is a linear, branched, or cyclic aliphatic $C_1$-$C_{12}$ or $C_1$-$C_6$ group, in addition in all aforementioned definitions $R_4$ is preferably a saturated and unsubstituted hydrocarbon group; $R_4$ preferably only comprises hydrogen and carbon atoms; preferably $R_4$ is methyl or ethyl;

$R_5$ is selected from the group consisting of linear, branched, or cyclic aliphatic groups, aromatic groups, and heteroaromatic groups as well as combinations thereof preferably in all aforementioned definitions $R_5$ has 1-12 carbon atoms or 1-6 carbon atoms, in particular $R_5$ is a linear, branched, or cyclic aliphatic $C_1$-$C_{12}$ or $C_1$-$C_6$ group, in addition in all aforementioned definitions $R_5$ is preferably a saturated and unsubstituted hydrocarbon group; $R_5$ preferably only comprises hydrogen and carbon atoms; $R_5$ is methyl or ethyl;

$R_6$ is selected from the group consisting of linear, branched, or cyclic aliphatic groups, and aromatic groups as well as combinations thereof, preferably in all aforementioned definitions $R_6$ has 1-12 carbon atoms or 1-6 carbon atoms, in particular $R_6$ is a linear, branched, or cyclic aliphatic $C_1$-$C_{12}$ or $C_1$-$C_6$ group, in addition in all aforementioned definitions $R_6$ is preferably a saturated and unsubstituted hydrocarbon group; $R_6$ is methyl or ethyl;

$R_9$ is a protective group, or is selected from the group consisting of compounds comprising an electron withdrawing group such as carboxyl/carbonyl; carbamates and heteroaromatic groups as well as combinations thereof, preferably in all aforementioned definitions $R_9$ has 1-12 carbon atoms or 1-6 carbon atoms and includes heteroatoms, in particular $R_9$ is a linear, branched, or cyclic aliphatic $C_1$-$C_{12}$ or $C_1$-$C_6$ group; The protective groups can be N-phospinoyl, N-carbamoyl or R-carbonyl such as tert-trifluoroacetyl (TFA), formyl; or R-carboxyl such as tert-butoxycarbonyl (Boc), methoxycarbonyl, 2,2,2-Trichlorethoxycarbonyl (Troc), benzyloxycarbonyl (Cbz) and Fluorenylmethyloxycarbonyl (Fmoc); Within the context of the present invention, the preferred protective groups are protective groups having electron withdrawing properties, particularly preferred are protective groups having carboxyl or carbonyl groups.

$R_{12}$ is selected from the group consisting of H, linear, branched, or cyclic aliphatic groups, aromatic groups, and heteroaromatic groups as well as combinations thereof, preferably in all aforementioned definitions $R_{12}$ has 1-12 carbon atoms or 1-6 carbon atoms, in particular $R_{12}$ is a linear, branched, or cyclic aliphatic $C_1$-$C_{12}$ or $C_1$-$C_6$ group, in addition in all aforementioned definitions, $R_{12}$ preferably only comprises hydrogen and carbon atoms; preferably $R_{12}$ is cyclopropyl;

$R_{13}$ is selected from the group consisting of a chain of amino acids, such as e.g. natural amino acids, bicyclic proline, Cert-leucin, or any other unnatural amino acids containing aliphatic, cyclic aliphatic, aromatic and heteroaromatic moieties, for example the compounds of Formula 8a and 8b; linear, branched, or cyclic aliphatic groups, aromatic groups, heteroaromatic groups as well as combinations thereof, and —CH($R_{14}$)-$R_{15}$, wherein $R_{14}$ is selected from the group consisting of linear, branched, or cyclic aliphatic groups, aromatic groups, heteroaromatic groups as well as combinations thereof and $R_{15}$=—$CO_2R_{14}$ or —C(O)NHR$_{14}$; As used herein, the expression "chain of amino acids" can be a small peptide such as a peptide as in compound 8a, in particular a peptide comprising 2-10 amino acids.

In the first stage (i) of the processes of the first aspect, a compound of Formula 2/2a is provided.

The compound according to Formula 2/2a can be prepared by applying standard synthesis methods (see e.g. Eur. J. Org. Chem. 2005, 2599-2606 and "March's advanced organic chemistry" Ed. 5. p. 1185-1187). Preferably, $R_2$ has one or more stereocenters, preferably the stereocenter is in α-position of the imine-N atom.

The compound according to Formula 2/2a can be used in stereochemically pure form, based on synthesis from enantiomerically-enriched building blocks. Preferably, the compound of Formula 2/2a has an enantiomeric/stereochemical purity of at least 70%, preferably 80%, further preferred 90%, even further preferred 95% and most preferably more than 97% based on the total amount of all isomers of Formula 2/2a. The stereochemical purity/enantiomeric purity, referred to in the context of the present invention, can for example be determined by appropriate nuclear magnetic resonance (NMR) experiments as known in the art or by chiral high performance liquid chromatography (HPLC) as known in the art.

In the second stage (ii), the compound of Formula 2, e.g. 2a, is brought into contact with the compound of Formula 3 in the presence of an acid, such as a Lewis acid, thereby obtaining a compound of Formula 4/4a or 4'/4b', depending on whether $R_2$ has a stereogenic center, such as a stereogenic center in α-position of the imine-N atom, with one stereoconfiguration being present in excess, wherein the compound of Formula 4/4a is obtained if $R_2$ has a stereogenic C-atom, preferably in α-position of the imine N-atom, in the compound of Formula 2 and the compound of Formula 4'/4b' is obtained if $R_2$ does not have a stereogenic C-atom, such as a stereogenic C-atom in α-position of the imine N-atom, or,

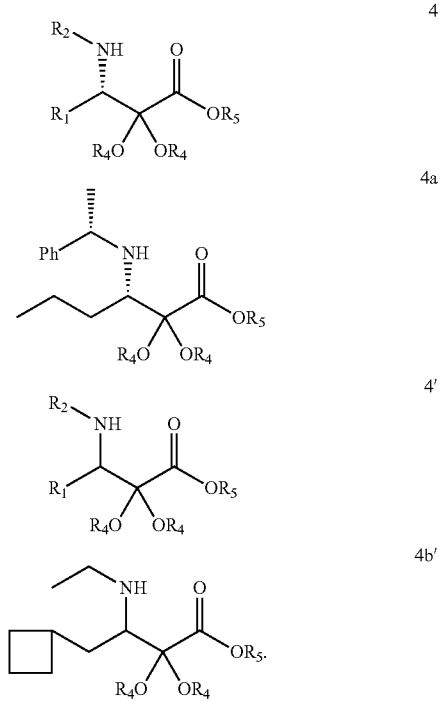

In one embodiment, the compound of Formula 2 is reacted with the compound of Formula 3. In another embodiment, the compound of Formula 2a is reacted with the compound of Formula 3. Suitable acids such as Lewis acids and solvents are described in the general part below.

Preferably, no chiral Lewis acid is used in stage (ii).

In the third stage (iii) the following steps are conducted: (a) deprotecting the compound of Formula 4/4a or 4'/4b' in order to provide an $NH_2$-group and (b) protecting the obtained $NH_2$-group in order to provide a compound of Formula 5/5a or 575b'

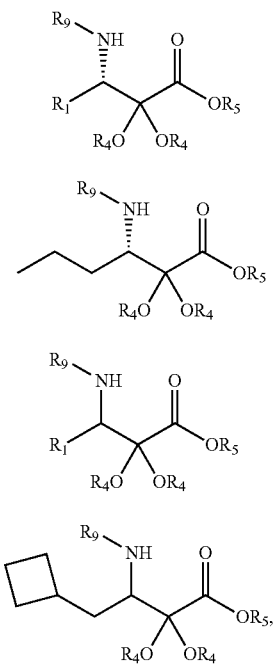

5

5a

5'

5b' wherein in the compound of Formula 5a/5b' and 5/5' $R_9$ is a protective group, such as tert-butoxycarbonyl (Boc) or benzyloxycarbonyl (Cbz), or $R_9$ is as defined above. Depending on the protective group, the third stage can be performed stepwise or in a one-pot procedure, thus saving time and solvents.

In the fourth stage (iv) the following steps are conducted: (a) hydrolyzing the compound of Formula 5/5a or 5'/5b' in order to substitute the $OR_5$-group with an OH-group and (b) performing an amine coupling reaction of the compound of Formula 5/5a with cyclopropylamine/$H_2NR_{12}$ in the presence of one or more coupling agents in order to provide a compound of Formula 6/6a

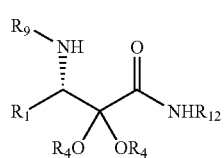

6

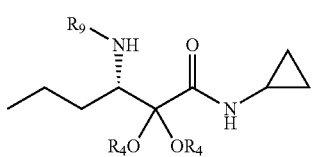

6a or reacting the compound of Formula 5'/5b' with an ammonia source under amine coupling conditions to provide a compound of Formula 6'/6b'

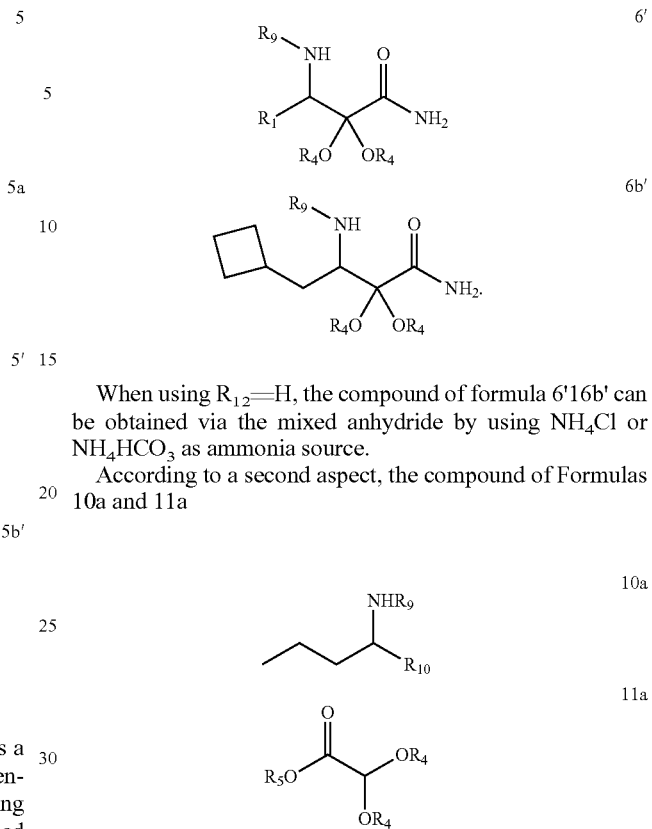

When using $R_{12}$=H, the compound of formula 6'16b' can be obtained via the mixed anhydride by using $NH_4Cl$ or $NH_4HCO_3$ as ammonia source.

According to a second aspect, the compound of Formulas 10a and 11a

10a

11a are used as starting materials.

In the context of the second aspect, $R_9$ is a protective group, such as tert-butoxycarbonyl (Boc), N-carbamoyl-, N-formyl, N-phospinoyl- or benzyloxycarbonyl (Cbz), preferably tert-butoxycarbonyl (Boc) or benzyloxycarbonyl (Cbz); $R_4$ and $R_5$ are independently methyl or ethyl; and $R_{10}$ is $SO_2Ar$ (Ar=aryl) such as $SO_2Ph$, or OMe. The synthesis of compounds according to Formula 10a is for example described in B. Yin et al. "Recent Applications of α-Amido Sulfones as in situ Equivalents of Activated Imines for Asymmetric Catalytic Nucleophilic Addition Reactions", Synthesis, 2010, 21, 3583-3595 or for $R_{10}$=OMe in P. Gizecki et al. "Diastereoselective preparation of novel tetrahydrooxazinones via heterocycloaddition of N-Boc, O-Me-acetals", Tetrahedron Letters, 2004, 45, 9589-9592.

In the first stage (i) of the processes of the second aspect, a compound of Formula 10a is provided.

In the second stage (ii), the compound of Formula 10a is brought into contact with the compound of Formula 11a in the presence of a strong base in order to provide the enolate of 11a and the imine of 10a, such as lithium diisopropylamide, thereby obtaining a compound of Formula 5a' as racemic mixture of enantiomers

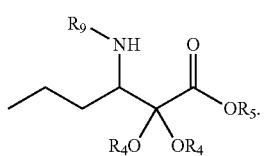

5a'

In a third stage (iii), the following steps are conducted: (a) hydrolyzing the compound of Formula 5a' in order to substitute the $OR_5$-group with an OH-group and (b) performing an amine coupling reaction with cyclopropylamine in the presence of one or more coupling agents in order to provide a compound of Formula 6a'

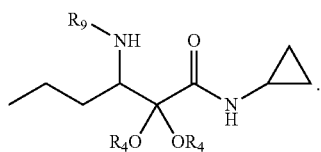

6a'

For example, the compound of formula 6a' can be obtained by saponification and amidation under standard conditions (KOH/MeOH and TBTU or DIC/HOBt and cyclopropylamine).

According to a third aspect, the intermediates of Formula 6/6a and 6a' can be further reacted as described in the following. The definition of the R-groups is the same as given in the first and second aspect, respectively.

In a first stage (i) the compound of Formula 6/6a or 6'/6a'/6b' as prepared above can be deprotected in order to provide (a) a compound of Formula 7/7a (starting from compound 6/6a), or (b) a compound of Formula 7'/7a'/7b', see formulas below (starting from Formula 6'/6a'/6b'), and separating the racemic mixture 7a' to provide a compound of Formula 7a.

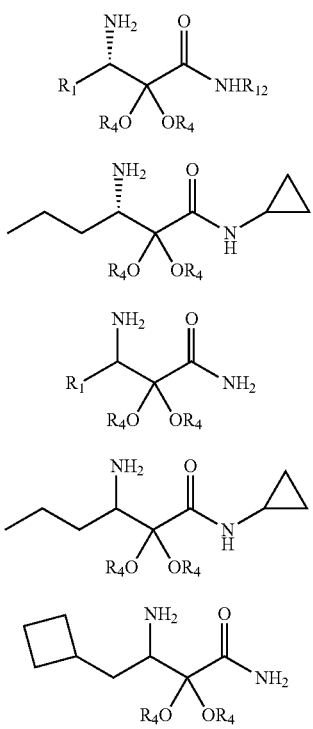

According to a fourth aspect, the compound of Formula 7/7a or 7'/7b' as prepared according to the above aspects with the definitions of the R-groups as given in the respective aspects, can be further reacted as follows:

The compound of Formula 7/7a or 7'/7b' can be brought into contact with a compound of Formula $R_{13}$COOH (with $R_{13}$ as defined above) or 8a/8b

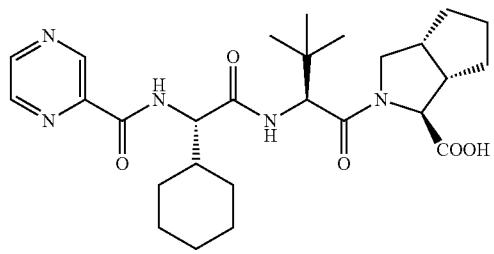

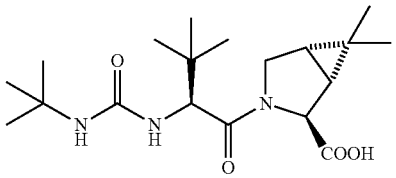

in the presence of one or more coupling agents, thereby obtaining a compound of Formula 9/9a or 9'/9b',

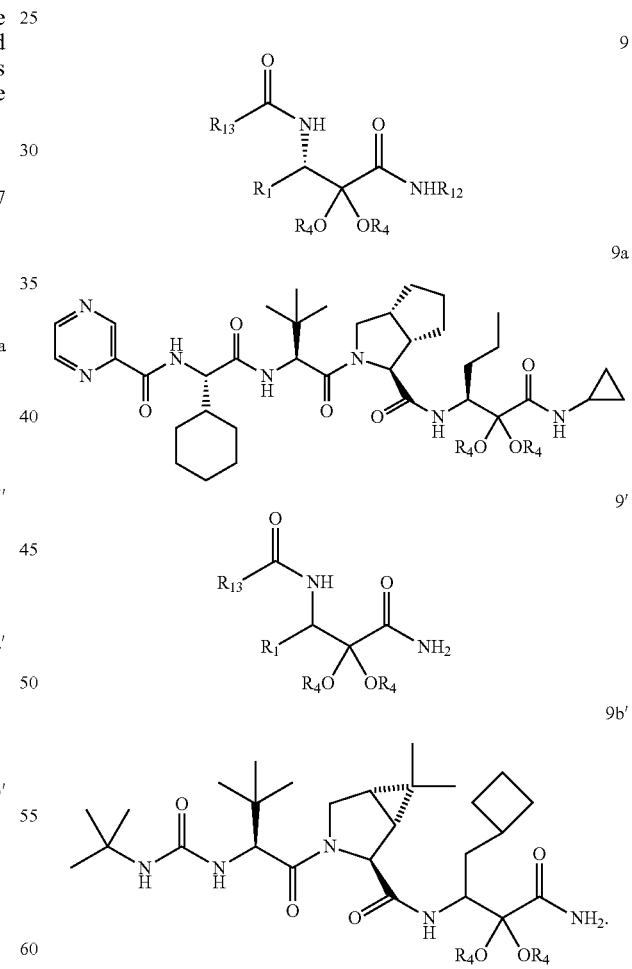

In a next stage, the compound of Formula 9a/9b' can be deprotected in the presence of an acid thereby obtaining telaprevir of Formula 1/boceprevir according to Formula 25, or a pharmaceutically acceptable salt or solvate thereof. During the deprotection step, the presence of a ketone such as acetone is preferred. Likewise the compounds of Formula 9/9' can be deprotected in the presence of an acid thereby obtaining the compounds of Formulas

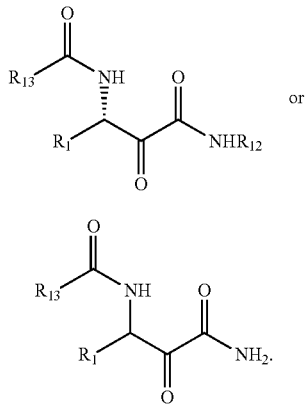

According to the invention, an oxidation reaction in the last step of the preparation of telaprevir can be avoided by performing an acetal deprotection step as the last synthesis step as described above. The thus obtained telaprevir is preferably essentially free of oxidative side-products and preferably contains oxidative side products in amounts of less than 0.10 area % as determined by HPLC or LC-MS analysis (see Example 26).

According to a preferred aspect, the invention provides telaprevir which is essentially free of 15a and 21a and 16a.

According to a preferred aspect, the invention provides telaprevir containing compound 7a and 9a in an amount of less than 0.15 area %.

According to a fifth aspect, the compounds of Formula

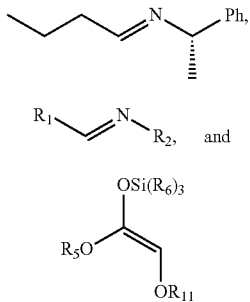

are used as starting materials. Furthermore, the definitions for groups $R_1$-$R_{13}$ below can be applied in the fifth aspect:

$R_1$ is selected from the group consisting of linear, branched, or cyclic aliphatic groups, aromatic groups (aromatic groups are less preferred), and heteroaromatic groups as well as combinations thereof, preferably in all aforementioned definitions $R_1$ has 1-12 carbon atoms or 1-6 carbon atoms, in particular $R_1$ is a linear, branched, or cyclic aliphatic $C_1$-$C_{12}$ or $C_1$-$C_6$ group, in addition in all aforementioned definitions $R_1$ is preferably a saturated and unsubstituted hydrocarbon group such as an alkyl group; preferably $R_1$ is a propyl group;

$R_2$ is selected from the group consisting of linear or branched arylalkyl groups, aromatic groups, carbamates and heteroaromatic groups as well as combinations thereof; preferably in all aforementioned definitions $R_2$ has 1-12 carbon atoms or 1-6 carbon atoms, in particular $R_2$ is an arylalkyl group, preferably a methylene aromatic group, preferably benzylic, $C_7$-$C_{12}$ group, in addition in all aforementioned definitions $R_2$ is preferably an unsubstituted hydrocarbon group, i.e. a group that only comprises hydrogen and carbon atoms; Preferably, $R_2$ has one or more stereocenters, preferably the stereocenter is in α-position of the imine-N atom; preferably $R_2$ is $CH(CH_3)Ph$, preferably $R_2$ is $CH(CH_3)Ph$ with (S)-configuration;

$R_5$ is selected from the group consisting of linear, branched, or cyclic aliphatic groups, aromatic groups, and heteroaromatic groups as well as combinations thereof, preferably in all aforementioned definitions $R_5$ has 1-12 carbon atoms or 1-6 carbon atoms, in particular $R_5$ is a linear, branched, or cyclic aliphatic $C_1$-$C_{12}$ or $C_1$-$C_6$ group, in addition in all aforementioned definitions $R_5$ is preferably a saturated and unsubstituted hydrocarbon group; preferably $R_5$ is methyl or ethyl;

$R_6$ is selected from the group consisting of linear, branched, or cyclic aliphatic groups, and aromatic groups, as well as combinations thereof, preferably in all aforementioned definitions $R_6$ has 1-12 carbon atoms or 1-6 carbon atoms, in particular $R_6$ is a linear, branched, or cyclic aliphatic $C_1$-$C_{12}$ or $C_1$-$C_6$ group, in addition in all aforementioned definitions $R_6$ is preferably a saturated and unsubstituted group; more preferably $R_6$ is methyl or ethyl;

$R_9$ is a protective group or is selected from the group consisting of compounds comprising an aromatic moiety and an electron withdrawing group such as carboxyl/carbonyl, carbamates and heteroaromatic groups as well as combinations thereof, preferably in all aforementioned definitions $R_9$ has 1-12 carbon atoms or 1-6 carbon atoms, in particular $R_9$ is a linear, branched, or cyclic aliphatic $C_1$-$C_{12}$ or $C_1$-$C_6$ group; The protective groups can be R-carbonyl such as tert-trifluoroacetyl (TFA), formyl groups; or R-carboxyl such as butoxycarbonyl (Boc), Troc, methoxycarbonyl, benzyloxycarbonyl (Cbz);

$R_{11}$ is selected from the group consisting of linear, branched, or cyclic aliphatic groups, arylalkyl groups, aromatic groups, and heteroaromatic groups as well as combinations thereof, preferably in all aforementioned definitions $R_{11}$ has 1-12 carbon atoms or 1-6 carbon atoms, in particular $R_{11}$ is a linear, branched, or cyclic aliphatic $C_1$-$C_{12}$ or $C_1$-$C_6$ group, in addition in all aforementioned definitions $R_{11}$ is preferably a hydrocarbon (such as phenyl)-silyl group; $R_{11}$ can for example be: tert-butyldimethylsilyl (TBS), tert-butyldiphenylsilyl (TBDPS), p-Methoxybenzyl (PMB), triisopropylsilyl (TIPS), or benzyl (Bn); In the compound of Formulas 12/13/14a/15a, $R_{11}$ is tert-butyldimethylsilyl (TBS), or benzyl (Bn).

$R_{12}$ is selected from the group consisting of H, linear, branched, or cyclic aliphatic groups, aromatic groups, and heteroaromatic groups as well as combinations thereof, preferably in all aforementioned definitions $R_{12}$ has 1-12 carbon atoms or 1-6 carbon atoms, in particular $R_{12}$ is a linear, branched, or cyclic aliphatic $C_1$-$C_{12}$ or $C_1$-$C_6$ group, in addition in all aforementioned definitions $R_{12}$ is preferably a saturated and unsubstituted hydrocarbon group; preferably $R_{12}$ is cyclopropyl;

$R_{13}$ is selected from the group consisting of a chain of amino acids, such as e.g. natural amino acids, bicyclic proline, tert-leucin, or any other unnatural amino acids containing aliphatic, cyclic aliphatic, aromatic and heteroaromatic moieties, for example the compounds of Formula 8a and 8b; linear, branched, or cyclic aliphatic groups, aromatic groups, heteroaromatic groups as well as combinations thereof, and —CH($R_{14}$)—$R_{15}$, wherein $R_{14}$ is selected from the group consisting of linear, branched, or cyclic aliphatic groups, aromatic groups, heteroaromatic groups as well as combinations thereof and $R_{15}$=—$CO_2R_{14}$ or —C(O)NH$R_{14}$;

In a first stage (i), the compound of Formula 2/2a is provided. The comments as to the compound of Formula 2/2a as provided in the above aspects also apply here.

In a second stage (ii), the compound of Formula 2/2a is brought into contact with a compound of Formula 12 in the presence of a Lewis acid, thereby obtaining a compound of Formula 13/13a

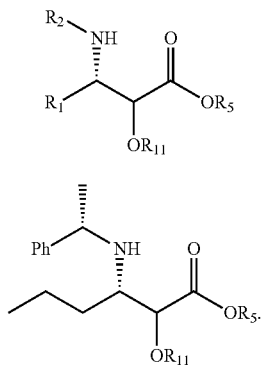

In order to provide a stereoselective reaction of the compound of Formula 2, e.g. 2a, with the compound of Formula 12, $R_2$ in the compound of Formula 2/2a has to have one stereogenic center, preferably in α-position to the imine-N atom, with one stereoconfiguration being present in excess. If no such stereogenic center is present in α-position to the imine-N atom, the reaction will not provide a large excess of a preferred diastereomer.

In an optional third stage (iii), the following steps are performed: (a) deprotecting the compound of Formula 13/13a in order to provide an NH$_2$-group and (b) protecting the obtained NH$_2$-group in order to provide a compound of Formula 23/23a

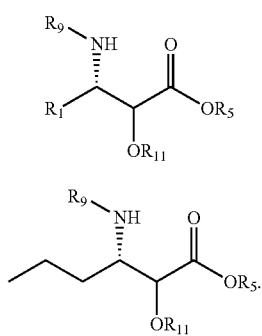

In a fourth stage (iv) the following steps are performed: (a) hydrolyzing the compound of Formula 13/23, 13a/23a in order to substitute the OR$_5$-group with an OH-group and (b) performing an amine coupling reaction with cyclopropylamine/H$_2$NR$_{12}$ in the presence of one or more coupling agents in order to provide a compound of Formula 14 or 24/14a or 24a:

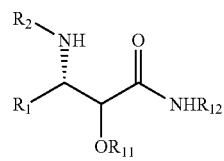

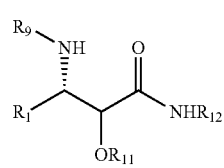

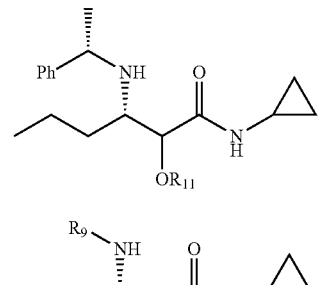

In a fifth stage (v), the compound of Formula 14/24/14a/24a can be deprotected in order to provide a compound of Formula 15/15a

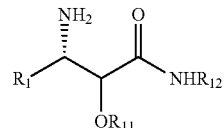

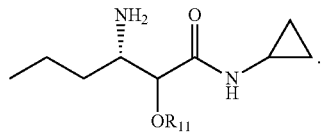

According to a sixth aspect, the compounds of Formulas 10a and 17a

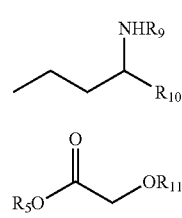

are used as starting materials.

In the sixth aspect, the definitions of the R-groups can be as defined in the second (in particular definitions for $R_9$ and $R_{10}$) and fifth aspect (in particular definitions for $R_{11}$ and $R_5$). In particular, $R_9$ can be a protective group, such as tert-butoxycarbonyl (Boc), N-carbamoyl-, N-formyl, N-phospinoyl- or benzyloxycarbonyl (Cbz) and $R_{10}$ is $SO_2Ar$ (Ar=aryl) such as $SO_2Ph$, or OMe; $R_5$ is methyl or ethyl and $OR_{11}$ is tertbutyldimethylsiloxyl.

In a first stage (i), the compound of Formula 10a is provided.

In a second stage (ii), the compound of Formula 10a is brought into contact with a compound of Formula 17a in the presence of a strong base such as lithium diisopropylamide in order to provide the enolate of 17a and generate the imine, thereby obtaining a compound of Formula 18a' as racemic mixture of diastereomers.

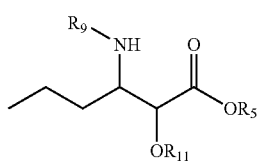

18a'

In a third stage (iii), the following steps can be conducted: (a) hydrolyzing the compound of Formula 18a' in order to substitute the $OR_5$-group with an OH-group and (b) performing an amine coupling reaction with cyclopropylamine in the presence of one or more coupling agents in order to provide a compound of Formula 19a'

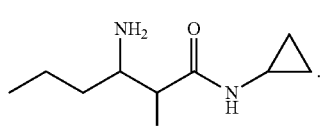

19a'

In a fourth stage (iv) the compound of Formula 19a' can be deprotected in order to provide a compound of Formula 15a'

15a'

In a fifth stage (v) the racemic mixture of the compound of Formula 15a' can be separated in order to provide a compound of Formula 15a 15a According to a seventh aspect, the compound of Formula 15/15a as prepared according to the above aspects with the definitions of the R-groups as given in the respective aspects can be further reacted as follows:

The compound of Formula 15/15a can be brought into contact with an organic acid of Formula $R_{13}COOH$ ($R_{13}$ can for example be defined as in the first aspect; $R_{11}$ and $R_{12}$ can for example be defined as in the fifth aspect) or 8a

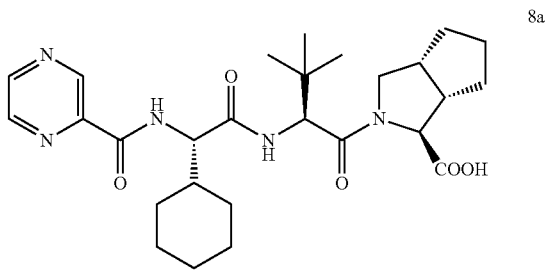 [SMILES: CC(C)(C)[C@H](NC(=O)[C@@H](NC(=O)c1cnccn1)C1CCCCC1)C(=O)N1C[C@@H]2CCC[C@@H]2[C@H]1C(=O)O]

8a in the presence of one or more coupling agents, thereby obtaining a compound of Formula 16/16a,

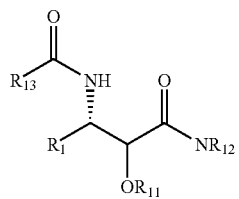

16

16a

In a next stage, the protecting group $R_{11}$ can be cleaved, thereby obtaining a compound according to Formula 21/21a

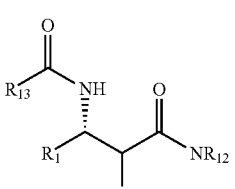

21

-continued

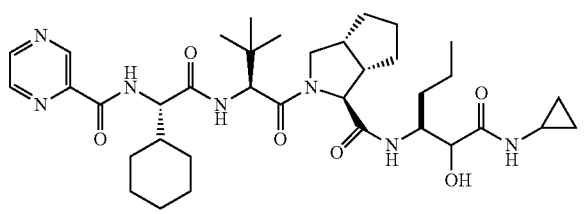

21a

In a further stage the compound according to Formula 21a can be oxidized, thereby obtaining telaprevir according to Formula 1, or a pharmaceutically acceptable salt or solvate thereof, or a compound of formula 26:

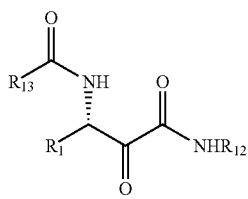

26

A further aspect refers to compounds according to Formulas 6 and 6', preferably obtainable or obtained by carrying out the respective processes as described above:

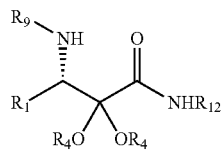

6

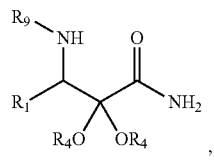

6' wherein $R_1$ is selected from the group consisting of linear, branched, or cyclic aliphatic groups, aromatic groups, and heteroaromatic groups as well as combinations thereof, preferably $R_1$ is a propyl group;

$R_4$ and $R_{12}$ are independently selected from the group consisting of linear, branched, or cyclic aliphatic groups, aromatic groups, and heteroaromatic groups as well as combinations thereof, preferably $R_4$ is methyl or ethyl and $R_{12}$ is cyclopropyl;

$R_9$ is a protective group or is selected from the group consisting of linear, branched, or cyclic aliphatic groups, aromatic groups, and heteroaromatic groups as well as combinations thereof, preferably $R_9$ is a protective group such as tert-butoxycarbonyl (Boc), formyl; or benzyloxycarbonyl (Cbz);

preferred is a compound of Formula 6a:

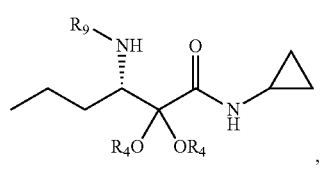

6a wherein $R_4$ is methyl or ethyl; and $R_9$ is a protective group such as tert-butoxycarbonyl (Boc) or benzyloxycarbonyl (Cbz). The R-groups can also be chosen as described in the context of the preparation of the compounds of Formula 6/6a in the above aspects.

The compound according to Formula 6/6a has a high purity, preferably has a stereochemical purity of at least 99%. The impurities can be determined by HPLC-MS or NMR as described above.

A further aspect refers to a compound according to Formula 14, 24, preferably obtainable or obtained by carrying out the respective processes as described above:

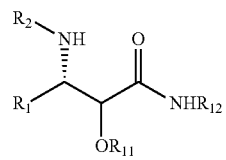

14

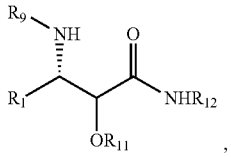

24 wherein $R_1$ is selected from the group consisting of linear, branched, or cyclic aliphatic groups, aromatic groups, and heteroaromatic groups as well as combinations thereof, preferably $R_1$ is a propyl group;

$R_{11}$ and $R_{12}$ are independently selected from the group consisting of linear, branched, or cyclic aliphatic groups, aromatic groups, and heteroaromatic groups as well as combinations thereof, preferably $R_{11}$ is a hydrocarbon-silyl group such as tert-butyldimethylsilyl (TBS) or benzyl (Bn) and $R_{12}$ is cyclopropyl;

$R_2$ is selected from the group consisting of hydrogen; linear or branched arylalkyl groups, aromatic groups, carbamates and heteroaromatic groups as well as combinations thereof, preferably $R_2$ is $CH(CH_3)Ph$, preferably $R_2$ is $CH(CH_3)Ph$ with (S)-configuration; and $R_9$ is a protective group or is selected from the group consisting of linear, branched, or cyclic aliphatic groups, aromatic groups, and heteroaromatic groups as well as combinations thereof, preferably $R_9$ is a protective group such as tert-butoxycarbonyl (Boc), formyl; or benzyloxycarbonyl (Cbz); preferably a compound of Formula 14a, or 24a:

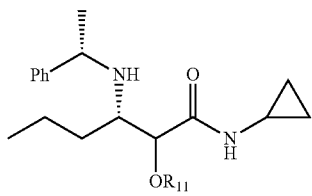

14a

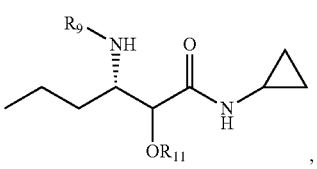

24a wherein $R_9$ is a protective group such as tert-butoxycarbonyl (Boc) or benzyloxycarbonyl (Cbz); $R_{11}$ is a hydrocarbon-silyl group such as tert-butyldimethylsilyl (TBS), tert-butyldiphenylsilyl (TBDPS), p-methoxybenzyl (PMB), triisopropylsilyl (TIPS), or benzyl (Bn). The R-groups can also be chosen as described in the context of the preparation of the compounds of Formula 14/24/14a/24a in the above aspects.

The compound according to Formula 14a/24a has a high purity, preferably has a stereochemical purity of at least 99%. The impurities can be determined by HPLC-MS or NMR as described above.

A further aspect refers to a compound according to Formula 7a, preferably obtainable or obtained by carrying out the respective processes as described above:

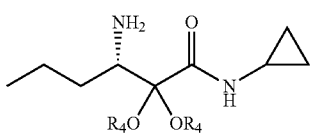

7a wherein $R_4$ is methyl or ethyl.

The compound according to Formula 7a has a high purity, preferably has a stereochemical purity of at least 99%. The impurities can be determined by HPLC-MS or NMR as described above.

A further aspect refers to a compound according to Formula 9 or 9', preferably obtainable or obtained by carrying out the respective process/processes as described above:

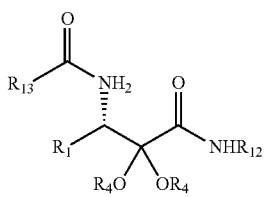

9

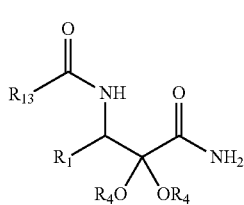

9' wherein $R_1$ is selected from the group consisting of linear, branched, or cyclic aliphatic groups, aromatic groups, and heteroaromatic groups as well as combinations thereof;

$R_{13}$ is selected from the group consisting of a chain of amino acids, such as e.g. natural amino acids, bicyclic proline, tert-leucin, or any other unnatural amino acids containing aliphatic, cyclic aliphatic, aromatic and heteroaromatic moieties; linear, branched, or cyclic aliphatic groups, aromatic groups, heteroaromatic groups as well as combinations thereof, and —CH($R_{14}$)—$R_{15}$, wherein $R_{14}$ is selected from the group consisting of linear, branched, or cyclic aliphatic groups, aromatic groups, heteroaromatic groups as well as combinations thereof and $R_{15}$=—CO$_2R_{14}$ or —C(O)NHR$_{14}$; As used herein, the expression "chain of amino acids" can be a small peptide such as a peptide as in compound 8a/8b, in particular a peptide comprising 2-10 amino acids.

$R_4$ and $R_{12}$ are independently selected from the group consisting of linear, branched, or cyclic aliphatic groups, aromatic groups, and heteroaromatic groups as well as combinations thereof, preferably $R_4$ is methyl or ethyl;

preferred is (are) a compound(s) of Formula 9a and 9b'

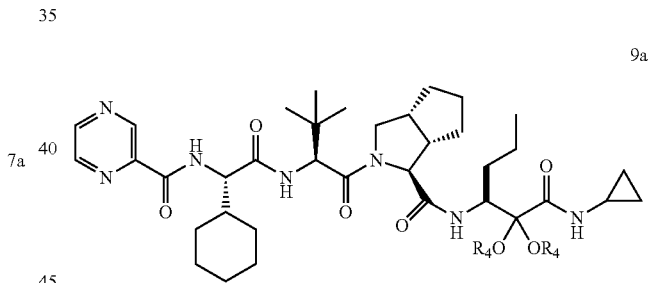

9a

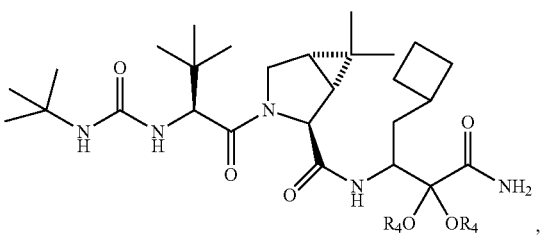

9b' wherein $R_4$ is methyl or ethyl; The R-groups can also be chosen as described in the context of the preparation of the compounds of Formula 9/9a/9b' in the above aspects.

The compound according to Formula 9a has a high purity, preferably has a stereochemical purity of at least 99%. The impurities can be determined by HPLC-MS or NMR as described above.

A further aspect refers to a compound according to Formula 16, preferably obtainable or obtained by carrying out the process as described above:

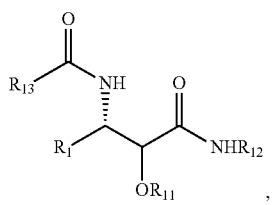

wherein $R_1$ is selected from the group consisting of linear, branched, or cyclic aliphatic groups, aromatic groups, and heteroaromatic groups as well as combinations thereof;

$R_{13}$ is selected from the group consisting of a chain of amino acids, such as e.g. natural amino acids, bicyclic proline, tert-leucin, or any other unnatural amino acids containing aliphatic, cyclic aliphatic, aromatic and heteroaromatic moieties; linear, branched, or cyclic aliphatic groups, aromatic groups, heteroaromatic groups as well as combinations thereof, and —CH($R_{14}$)—$R_{15}$, wherein $R_{14}$ is selected from the group consisting of linear, branched, or cyclic aliphatic groups, aromatic groups, heteroaromatic groups as well as combinations thereof and $R_{15}$=$CO_2R_{14}$ or —C(O)NHR$_{14}$; and $R_{11}$ and $R_{12}$ are independently selected from the group consisting of linear, branched, or cyclic aliphatic groups, aromatic groups, and heteroaromatic groups as well as combinations thereof, preferably $R_{11}$ is a hydrocarbon-silyl group such as tert-butyldimethylsilyl (TBS), or benzyl (Bn); preferably a compound of Formula 16a

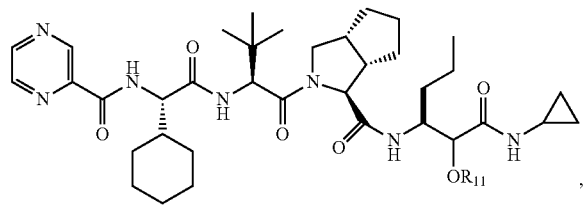

wherein $R_{11}$ is tert-butyldimethylsilyl (TBS), or benzyl (Bn). The R-groups can also be chosen as described in the context of the preparation of the compounds of Formula 16/16a in the above aspects.

The compound according to Formula 16/16a has a high purity, preferably has a stereochemical purity of at least 99%. The impurities can be determined by HPLC-MS or NMR as described above.

In the following, general aspects are described, which aspects refer to each of the aspects described herein.

Preferably, the stage/step of providing a compound includes dissolving said compound in a solvent or mixture of solvents. However, it is also possible to add said compound in pure form to the respective other compound(s) in the next stage/step.

A stage/step of bringing a compound into contact with a further compound can for example be carried out by dissolving said compounds either separately or as a mixture of compounds or by dissolving one of the compounds and adding to this solution the respective other compound. The order of combining the compounds can be chosen by a person skilled in the art.

Suitable solvents can be chosen by a person skilled in the art of common practice. Preferably, inert solvents are used. The term "inert solvent" refers to any solvents that do not react with the compounds described herein. Inert solvents suitable in this respect are commonly known. Solvents can be selected from the group consisting of ethylacetate, isopropyl acetate, dichloromethane, N,N-dimethylacetamide, dimethyl sulfoxide (DMSO), N-methylpyrrolidone, N,N-dimethylformamide, acetonitrile, methyl tert-butyl ether, tetrahydrofuran, 2-methyltetrahydrofuran, aromatic hydrocarbons such as toluene and, hydrocarbon solvents, for example hexane and heptane, alcohols, for example methanol and ethanol, and water.

THF or 2-methyltetrahydrofuran are preferably used for the formation of silyl enol ethers 3 and 12 and for the aldol addition relying on in situ imine formation, and as mixture with water for amine protection; dichloromethane, 2-methyltetrahydrofuran and toluene are preferably used for the aldol addition; EtOAc and ethanol are preferably used for hydrogenation; MeOH or EtOH and water mixtures were preferably used for saponification; dichloromethane and dimethylformamide were preferably used for amidation.

The addition of the imine and the silyl enol ether can be performed in the presence of an acid, such as a Lewis acid for example at a temperature of about 0° C. Particular suitable acids are Lewis acids like $MgBr_2Et_2O$, $BF_3Et_2O$ and $HBF_4$. It has been found in the context of the present invention that it is not required to use chiral boron reagents and the use of chiral boron reagents or chiral Lewis acids in general is not preferred according to the invention since it may only provide a slight increase in selectivity but purification may be significantly harder to achieve. The acid, such as Lewis acid, can for example be used in an amount of 1 to 2 equivalents based on the silyl enol ether compound. The imine and silyl enol ether can be used in equal amounts.

The addition of the imine and the silyl enol ether can for example be performed in dichloromethane, toluene or 2-methyltetrahydrofuran.

The addition of the imine generated in situ from 10 and the enolate from 11 or 17 can be performed at low temperatures, for example −78° C. in the presence of a strong base such as lithiumdiisopropylamide (LDA) which provides the enolate and imine. The reaction can for example be carried out in tetrahydrofurane.

The amine coupling reactions can for example be carried out in the presence of a base and one or more coupling agents selected from the group consisting of dicyclohexylcarbodiimide (DCC), diisopropylcarbodiimide (DIC), 1-ethyl-3-(3-dimethylaminopropyl)carbodiimide hydrochloride (EDC), 1-hydroxy-benzotriazole (HOBt) or 1-hydroxy-7-aza-benzotriazole (HOAt), O-Benzotriazole-N,N,N',N'-tetramethyl-uronium-hexafluoro-phosphate (HBTU), O-(7-Azabenzotriazol-1-yl)-N,N,N',N'-tetramethyluronium hexafluorophosphate (HATU), O-(6-Chlorobenzotriazol-1-yl)-N,N,N',N'-tetramethyluronium hexafluorophosphate (HCTU), O-(Benzotriazol-1-yl)-N,N,N',N'-tetramethyluronium tetrafluoroborate (TBTU), (benzotriazol-1-yl-oxytripyrrolidinophosphonium hexafluorophosphate) (PyBOP), substituted 1,3,5,2,4,6-trioxatriphosphorinane-2,4,6-trioxide and via the formation of a mixed anhydride using a chloroformate ester, pivaloyl chloride, mesyl chloride or similar reagents known to persons skilled in the art. Preferred coupling reagents for amidation of beta-amino acids are DIC/HOBt and TBTU; for the amide coupling reaction the preferred reagents are T3P, EDC/HOBt, DIC/HOBt and isobutyl chloroformate.

A preferred substituted 1,3,5,2,4,6-trioxatriphosphorinane-2,4,6-trioxide is a compound of Formula 22

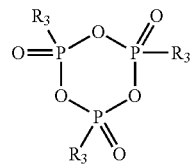

wherein $R_3$ is a saturated or unsaturated, branched, cyclic or linear, substituted or unsubstituted $C_{1-10}$ hydrocarbon compound, preferably, $R_3$ is n-propyl or phenyl. Example of compounds of Formula 8 are 2,4,6-tripropyl-1,3,5,2,4,6-trioxatriphosphorinane-2,4,6-trioxide (T3P) and 2,4,6-triphenyl-1, 3,5,2,4,6-trioxatriphosphorinane-2,4,6-trioxide. If a compound of Formula 8 is used as coupling agent, it is preferred to use it as the only coupling agent.

However, it is also possible to use other coupling agents known in the art such as uronium coupling agents. For an overview of possible coupling reagents, reference is made to Han, S.-Y.; Kim, Y.-A. Tetrahedron 2004, 60, 2447-2467.

The amount of coupling agent(s) can be from 0.8 to 6 equivalents, preferably from 0.9 to 4 equivalents, further preferred from 1 to 2 equivalents, based on the total amount of the acid compound that is to be coupled. If more than one coupling agent is used, the different types of coupling agents can be used in the same or different amounts. Preferably, they are all used in an amount of more than 1 equivalent based on the amount of the acid compound. Further preferred, each coupling agent is used in an amount of 1 to 2 equivalents based on the total amount of the acid compound.

Suitable reaction temperatures for the reactions described herein can be chosen by a person skilled in the art. For example, the step of combining the coupling agent(s) with the other compounds can be carried out at 0° C. to room temperature (for example for a time of 1 minute to 1 hour) and the reaction can then be completed at 0° C. to 50° C. (for example for a time of 1 hour to 30 hours). Room temperature is defined herein as a temperature range of 20-25° C. Furthermore, reactions with strong bases such as lithiumdiisopropylamide or other types of reactions that include the use of reactive compounds are conducted at low temperatures of e.g. below −20° C., below −50° C. or at about −78° C.

The amounts of the compounds as used herein can be chosen by a person skilled in the art. If two compounds are reacted with each other to provide a product compound based on a stochiometric 1:1 ratio of the starting materials, the starting compounds (including all potentially present isomers) can for example each be used in an amount from 0.8 to 3 equivalents, preferably from 0.9 to 2.0 equivalents, preferably from 1.0 to 1.6 equivalents.

Suitable amount(s) of solvent(s) that is/are used in step (ii) can be chosen by a person skilled in the art. The use of lower amounts of solvents leading to higher concentrations may provide for a faster reaction rate.

Generally, all stages/steps can include the isolation of the respective product compounds. Suitable methods for isolating said compounds are known in the art and comprise for example the washing of the organic layer with an aqueous salt solution (e.g. brine), separation of the organic layer, drying of said organic layer and removal of the organic solvent in vacuo. Dependent on the specific conditions, the work-up may further include acid and/or base washes. Furthermore, the compounds may be purified by using flash chromatographic techniques. However, if a compound is subjected to subsequent stages/steps it is possible to continue directly with the next stage/step without isolation of said intermediate product compounds.

The oxidizing agents are known to someone skilled in the art, preferably the oxidizing agents are selected from the group of hypervalent iodine oxidants, comprising but not being limited to the Dess-Martin periodinane (1,1,1-Tris (acetyloxy)-1,1-dihydro-1,2-benziodoxol-3-(1H)-one) or IBX (2-iodoxybenzoic acid), or sodium hypochlorite in the presence of 2,2,6,6-tetramethylpiperidinyloxy free radical (TEMPO). Preferably, the oxidizing agent is sodium hypochlorite in the presence of 2,2,6,6-tetramethylpiperidinyloxy free radical (TEMPO).

Suitable amounts of oxidizing agent(s) can be chosen by a person skilled in the art according to common practice. For example, the oxidizing agent can be used in an amount of 0.9-2 equivalents, preferably, from 0.9 to 1.2 equivalents, based on the total amount of the compound to be oxidized. TEMPO can be used in catalytic amounts. Particularly suitable is a combination of a catalytic amount of TEMPO with KBr, $NaHCO_3$, and NaOCl in dichloromethane.

Stages/steps for providing pharmaceutically acceptable salts of telaprevir (1)/boceprevir can additionally comprise adding compounds such as acids to the reaction mixture which includes telaprevir/boceprevir.

Telaprevir/boceprevir or a pharmaceutically acceptable salt or solvate thereof can be isolated by precipitation and for example filtration, washing with solvent and drying. Prior to isolating the product, flash chromatographic techniques may be applied for purification. It is also preferred to isolate telaprevir/boceprevir, or a pharmaceutically acceptable salt or solvate thereof by crystallization.

Separation of racemic mixtures in the context of the present invention can for example be performed as follows: chiral HPLC, resolution of diastereomeric ammonium salts.

Separation of diastereomeric mixtures in the context of the present invention can for example be performed as follows: column chromatography or extraction of diastereoisomers showing different solubilities.

Strong bases that can be used in the context of the present invention are lithium diisopropylamide, LiTMP, LiHMDS.

Cleaving the dialkoxy ketal group in the compound of Formula 9a/9b in order to provide telaprevir/boceprevir can be performed by the addition of acid to an acetone/water mixture. Suitable examples include—but are not limited to—HCl, TFA or $H_2SO_4$.

Agents for deprotecting nitrogen-protecting groups are known to those skilled in the art; they can for example be selected from hydrogen on Pd/C (palladium on charcoal) and strong acids like TFA or HCl.

Hydrolyzing compounds such as esters can be performed according to methods known in the art.

Another aspect is the preparation of a pharmaceutical composition or pharmaceutical dosage form comprising telaprevir according to Formula 1 or boceprevir according to Formula 25, or a pharmaceutically acceptable salt or solvate thereof. The preparation comprises the process steps as described above and further comprises formulating the obtained telaprevir/boceprevir or a pharmaceutically acceptable salt or solvate thereof (the aforementioned compounds may also be referred to as active pharmaceutically compounds, API) into a pharmaceutical composition or pharmaceutical dosage form. The expression "a pharmaceutically acceptable salt or solvate thereof" as used herein always refers to both telaprevir and boceprevir. The step of formulating the API into a dosage form may be carried out by applying techniques known in the art. For example, the API can be formulated into tablets by using direct compression, dry or wet granulation processes, spray-coating processes or the like. The API may be formulated as an acid solution or as a solid.

The aldol addition reaction with silyl enol ethers can for example generally be carried out as follows: To the imine in a solvent, e.g. in CH$_2$Cl$_2$ (e.g. 0.2M), at low temperatures (e.g. below 10° C. or at 0° C. or below), is added an acid, such as a Lewis acid (e.g. 1-2 eq.) such as MgBr$_2$Et$_2$O or HBF$_4$OEt$_2$ and the mixture is stirred for e.g. 1-100 min, e.g. for 15 min. The silyl enol ether in a solvent (e.g. 1 eq.), e.g. in CH$_2$Cl$_2$ (1M), is added and the reaction is stirred at low temperatures (e.g. below 10° C. or at 0° C. or below), for e.g. 1-8 h. Brine can be added, layers can be separated and the aqueous layer can be extracted with CH$_2$Cl$_2$. The combined organic layers can be dried and the solvent can be removed under reduced pressure.

Purification can be performed by column chromatography (e.g. with silicagel, cyclohexane:EtOAc) to give the aldol adduct.

The one-pot aldol addition reaction with in situ generated imine and enolate can for example generally be carried out as follows: LDA in a suitable solvent (e.g. THF) is cooled to low temperatures (e.g. below −20° C., e.g. −50° C.) and a solution of a compound of Formula 10a and 17a/11a is added. The reaction is stirred at said low temperature (e.g. at −50° C.) for 0.5-2 h (e.g. 1 h), allowed to reach 0° C. over 1-3 h (e.g. 2 h), stirred at 0° C. for 1-3 h (e.g. 1 h) and then quenched by the addition of a saturated NH$_4$Cl solution. The layers can be separated, the aqueous layer can be extracted with a solvent, e.g. DCM. The combined organic layers can be dried and the solvent can be removed under reduced pressure. Column chromatography (e.g. silicagel, hexane:EtOAc) can be used for purification.

The invention also refers to telaprevir obtainable or obtained by the process described herein, preferably
(i) containing oxidative side products of telaprevir in less than 0.10 area % as determined by HPLC analysis,
(ii) being basically free of, preferably less than 0.10 area % as determined by HPLC analysis, 15a

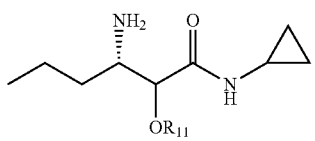

and 16a

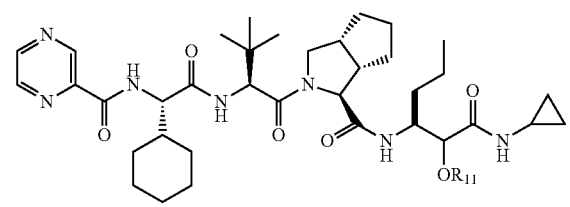

and/or
(iii) containing 7a

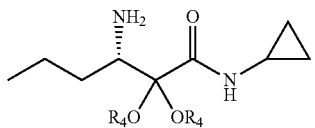

and 9a

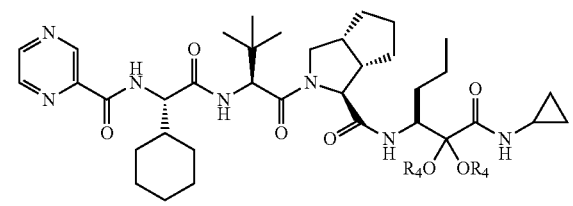

in less than 0.15 area % as determined by HPLC analysis.

Telaprevir obtainable or obtained by the method described herein has a high purity which may not be achieved when preparing telaprevir on a large scale by using prior art processes, since it may not be possible to purify said large amounts of telaprevir, e.g. 1 kg of telaprevir, by using common purification methods, as believed by the present inventors.

EXAMPLES

The following examples describe the present invention in detail, but are not to be construed to be in any way limiting for the present invention. In the examples below, the following abbreviations have the following meanings. Any abbreviations not defined have their generally accepted meaning. Unless otherwise stated, all temperatures are in degrees Celsius (° C.).

DMF: dimethylformamide; EtOAc: ethyl acetate; DCM/CH$_2$Cl$_2$: dichloromethane; TEMPO: (2,2,6,6-Tetramethylpiperidin-1-yl)-oxyl; Eq.: equivalents; rt: room temperature; Room temperature is defined herein as a temperature range of 20-25° C.; DIPEA: diisopropylethylamine; DIPET: diisopropyl ether; TBTU: O-(Benzotriazol-1-yl)-N,N,N',N'-tetramethyluronium tetrafluoroborate; Boc$_2$O: Di-tert-butyl dicarbonate; MS: molecular sieve; THF: tetrahydrofuran; MTBE: methyl tert-butyl ether; TBSCl: tert-butyldimethylsilyl chloride; LDA: lithium diisopropylamide; tol: toluene; TFA trifluoroacetic acid; Cbz: benzyloxycarbonyl; DIC: diisopropylcarbodiimide; EDC: (1-ethyl-3-(3-dimethylaminopropyl) carbodiimide hydrochloride); HOBt: 1-hydroxybenzotriazole, Et$_2$O: diethyl ether, CbzCl: benzyl chloroformate.

Example 1

(S,E)-N-butylidene-1-phenylethanamine (compound of Formula 2a)

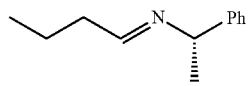

To a suspension of 10 g 3 Å MS in $CH_2Cl_2$ (150 mL) under $N_2$ at rt was added butyraldehyde (4.96 mL, 55 mmol) followed by (S)-(−)-1-phenylethylamine (6.45 mL, 50 mmol). The mixture was stirred at rt for 1.5 h, filtered over celite and the solvent removed under reduced pressure to give 9 g of the crude imine, which was used in the next step without further purification.

$^1$H NMR (500 MHz, $CDCl_3$): δ=7.67 (t, J=5.05 Hz, 1H), 7.28-7.23 (m, 4H), 4.21 (q, J=6.74 Hz, 1H), 2.18 (dt, J=7.48, 5.17 Hz, 2H), 1.53-1.49 (m, 2H), 1.42 (d, J=6.60 Hz, 3H), 0.87 (t, J=7.40 Hz, 3H).

$^{13}$C NMR (125 MHz, $CDCl_3$): δ=163.79, 145.09, 128.36, 126.72, 126.51, 69.70, 37.74, 24.59, 19.51, 13.72.

Example 2

2-(benzyloxy)acetic acid

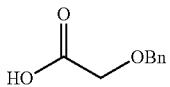

To a suspension of KOH (17.84 g, 118 mmol) in THF (200 mL) was added benzyl alcohol (42 mL, 424 mmol). After 1.5 h the mixture was heated to 50° C. for 1.5 h and cooled to rt afterwards. Chloroacetic acid (10 g, 106 mmol) was added and the mixture was heated to 80° C. After 1.5 h the mixture was cooled to rt and water and MTBE was added. The layers were separated, the aqueous layer was extracted with MTBE, the pH of the aqueous layer was adjusted to pH=2 with 6N HCl and extracted with MTBE. The extracts of the acidic layer were dried and the solvent removed under reduced pressure to give 12.4 g of the crude product.

$^1$H NMR (500 MHz, $CDCl_3$): δ=7.37 (m, 5H), 4.66 (s, 2H), 4.15 (s, 2H) $^{13}$C NMR (125 MHz, $CDCl_3$): δ=136.45, 128.63, 128.31, 128.12, 73.57, 66.61.

Example 3 methyl 2-(benzyloxy)acetate

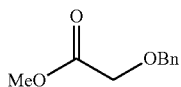

2-(benzyloxy)acetic acid (11.5 g, 69.2 mmol) in methanol (69 mL) with a catalytic amount of concentrated sulfuric acid was heated under reflux for 16 h. The reaction was cooled to rt and water and MTBE were added. The aqueous layer was extracted with MTBE and the combined organic layers were dried and the solvent removed under reduced pressure to give 7.9 g of the methyl ester.

$^1$H NMR (500 MHz, $CDCl_3$): δ=7.38-7.34 (m, 4H), 7.31 (m, 1H), 4.63 (s, 2H), 4.11 (s, 2H), 3.76 (s, 3H).

Example 4 methyl 2-hydroxyacetate

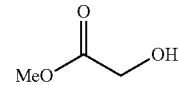

Glycolic acid (5 g, 65.7 mmol) in methanol (67 mL) with a catalytic amount of concentrated sulfuric acid was heated under reflux for 16 h. The reaction was cooled to rt and water and MTBE were added. The aqueous layer was extracted with MTBE and the combined organic layers were dried and the solvent removed under reduced pressure to give 4.1 g of the methyl ester.

$^1$H NMR (500 MHz, $CDCl_3$): δ=4.16 (s, 2H), 3.79 (s, 3H).

Example 5 methyl 2-((tert-butyldimethylsilyl)oxy)acetate

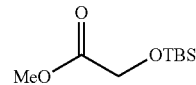

To a solution of methyl 2-hydroxyacetate (2.5 g, 27.7 mmol) in DMF (28 mL) was added imidazole (3.78 g, 55.5 mmol) followed by TBSCl (4.59 g, 30.47 mmol) and the mixture was stirred at rt for 4 h. Water was added and the mixture was extracted with 1:1 hexane:$Et_2O$. The combined organic layers were washed with water and brine, dried and the solvent removed under reduced pressure to give 6.2 g of the silyl ether.

$^1$H NMR (500 MHz, $CDCl_3$): δ=4.25 (s, 2H), 3.73 (s, 3H), 0.92 (s, 9H), 0.10 (s, 6H).

Example 6

General Procedure to Generate TMS Silyl Enol Ethers

To a solution of diisopropylamine (1.5 eq.) in THF (1.5M) at 0° C. under $N_2$ was added nBuLi (1.4 eq., 1.6M in hexane) and the mixture was stirred for 20 min. The LDA was cooled to −80° C. and TMSCl (1.4 eq.) was added followed by the methyl ester (1 eq.). The reaction was allowed to reach 0° C. over 3 h, brought to rt and stirred for 30 min. Pentane was added and the white precipitate filtered off over celite. The

Example 7

(E)-((2-((tert-butyldimethylsilyl)oxy)-1-methoxyvinyl)oxy)trimethylsilane (compound of Formula 12)

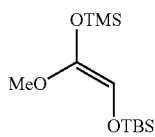

The synthesis was conducted using the general procedure of Example 6 with LiTMP (lithium tetramethylpiperidine) instead of LDA to generate selectively the (E)-silyl enol ether.

$^1$H NMR (500 MHz, C$_6$D$_6$): δ=5.71 (s, 1H), 3.53 (s, 3H), 1.00 (s, 9H), 0.15 (s, 9H), 0.14 (s, 6H).

Example 8

(E)-((2-(benzyloxy)-1-methoxyvinyl)oxy)trimethylsilane (compound of Formula 12)

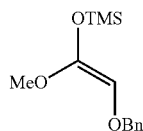

The synthesis was conducted using the general procedure of Example 6 with LiTMP instead of LDA to generate selectively the E-silyl enol ether.

$^1$H NMR (500 MHz, tol): δ=7.22 (m, 2H), 7.13 (m, 2H), 7.05 (m, 1H), 7.31 (m, 1H), 5.36 (s, 1H), 4.44 (s, 2H), 3.13 (s, 3H), 0.23 (s, 9H).

Example 9 trimethyl((1,2,2-trimethoxyvinyl)oxy)silane (compound of Formula 3)

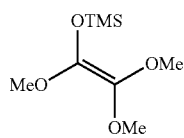

The synthesis was conducted using the general procedure of Example 6.

$^1$H NMR (500 MHz, C$_6$D$_6$): δ=3.45 (s, 3H), 3.44 (s, 3H), 3.37 (s, 3H), 0.25 (s, 9H).

Example 10 trimethyl((1,2,2-triethoxyvinyl)oxy)silane (compound of Formula 3)

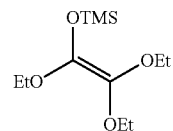

The synthesis was conducted using the general procedure of Example 6

$^1$H NMR (500 MHz, C$_6$D$_6$): δ=3.85 (q, J=7.04 Hz, 2H), 3.80 (q, J=7.02 Hz, 2H), 3.78 (q, J=7.05 Hz, 2H), 1.18 (t, J=7.10 Hz, 3H), 1.17 (t, J=7.08 Hz, 3H), 1.16 (t, J=7.08 Hz, 3H), 0.29 (s, 9H).

Example 10a

General Procedure for the Aldol Addition

To imine of Example 1 (1 eq.) in CH$_2$Cl$_2$ (0.2M) at 0° C. was added MgBr$_2$Et$_2$O (1.5 eq.) and the mixture was stirred for 15 min. The silyl enol ether of Example 6 (1 eq.) in CH$_2$Cl$_2$ (1M) was added and the reaction was stirred at 0° C. for 4 h. Brine was added, the layers were separated and the aqueous layer was extracted with CH$_2$Cl$_2$. The combined organic layers were dried and the solvent was removed under reduced pressure. Purification by column chromatography (silicagel, cyclohexane:EtOAc 10:1→3:1) gave the aldol adduct.

Example 11a (S)-methyl 2,2-dimethoxy-3-(((S)-1-phenylethyl)amino)hexanoate (compound of Formula 4a)

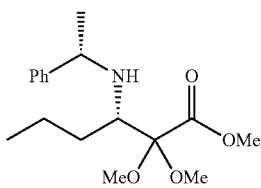 [SMILES: CCC[C@H](N[C@@H](C)c1ccccc1)C(OC)(OC)C(=O)OC]

To imine of Example 1 (4 g, 22.8 mmol) in CH$_2$Cl$_2$ (90 mL) at 0° C. was added MgBr$_2$Et$_2$O (8.84 g, 34.2 mmol) and the mixture was stirred for 15 min. The silyl enol ether of Example 9 (5 g, 24.2 mmol) in CH$_2$Cl$_2$ (15 mL) was added and the reaction was stirred at 0° C. for 4 h. Brine was added, layers were separated and the aqueous layer was extracted with CH$_2$Cl$_2$. The combined organic layers were dried and the solvent was removed under reduced pressure. Purification by column chromatography (silicagel, cyclohexane:EtOAc 10:1→3:1) gave the aldol adduct.

$^1$H NMR (500 MHz, CDCl$_3$): δ=7.33-7.28 (m, 4H), 7.21 (m, 1H), 4.23 (q, J=6.62 Hz, 1H), 3.82 (s, 3H), 3.27 (s, 3H), 3.19 (s, 3H), 2.73 (dd, J=10.08, 2.52 Hz, 1H), 1.49 (m, 1H), 1.37 (m, 1H), 1.27 (d, J=6.65 Hz, 3H), 1.09-0.97 (m, 2H), 0.67 (t, J=8.23 Hz, 3H).

$^{13}$C NMR (125 MHz, CDCl$_3$): δ=169.25, 146.29, 128.09, 127.33, 126.68, 106.08, 56.22, 55.96, 52.15, 50.61, 49.75, 33.36, 24.86, 19.66, 13.84.

Example 11b (S)-methyl 2,2-diethoxy-3-(((S)-1-phenylethyl) amino)hexanoate (compound of Formula 4a)

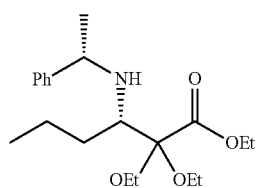 [SMILES: CCC[C@H](N[C@@H](C)c1ccccc1)C(OCC)(OCC)C(=O)OCC]

With BF$_3$OEt$_2$: (S,E)-N-butylidene-1-phenylethanamine (Example 1, 10.0 g, 57.0 mmol) was dissolved in 250 mL 2-methyltetrahydrofuran and cooled to 0° C. BF$_3$OEt$_2$ (7.0 mL, 57.0 mmol) was added to the mixture followed by a solution of trimethyl((1,2,2-triethoxyvinyl)oxy)silane (Example 10, 11.34 g, 45.6 mmol) in 80 mL 2-methyltetrahydrofuran, and the mixture was stirred at 0° C. After four hours, further imine (1.8 g, 10.2 mmol) and BF$_3$OEt$_2$ (1.2 mL, 9.7 mmol) were added and the mixture was stirred at 0° C. for further three hours. The volume of the mixture was halved by evaporation, water was added, the mixture was neutralized (pH=7.2) with 2N NaOH, and the phases were separated. Removal of the solvent in vacuo yielded 19.1 g crude (S)-ethyl 2,2-diethoxy-3-(((S)-1-phenylethyl)amino)hexanoate as a 85.15 (syn:anti) diastereomeric mixture.

With HBF$_4$OEt$_2$: (S,E)-N-butylidene-1-phenylethanamine (Example 1, 10.0 g, 57.0 mmol) was dissolved in 250 mL 2-methyltetrahydrofuran and cooled to 0° C. HBF$_4$OEt$_2$ (9.24 g, 57.0 mmol) was added to the mixture followed by a solution of trimethyl((1,2,2-triethoxyvinyl)oxy)silane (Example 10, 11.34 g, 45.6 mmol) in 80 mL 2-methyltetrahydrofuran, and the mixture was stirred at 0° C. for three hours and fifteen minutes. Water (400 mL) was added to quench the reaction, the mixture was neutralized (pH=7.6) with 10N NaOH, the phases were separated and the organic phase was extracted once more with further 400 mL water. Water (300 mL) and 2-methyltetrahydrofuran (50 mL) were added to the mixture, the pH was acidified (pH=5.6) with 2N HCl and the phases were separated. The organic phase was extracted with further 300 mL water and 50 mL 2-methyltetrahydrofuran and the solvent of the organic phase was removed in vacuo to yield 17.1 g crude (S)-ethyl 2,2-diethoxy-3-(((S)-1-phenylethyl)amino)hexanoate as a 86.14 (syn:anti) diastereomeric mixture.

Diastereomer separation in (S)-ethyl 2,2-diethoxy-3-(((S)-1-phenylethyl)amino)hexanoate by extraction (representative procedure):

A diastereomeric mixture of (S)-ethyl 2,2-diethoxy-3-(((S)-1-phenylethyl)amino)hexanoate (6.4 g, d.r.: 85:15) was dissolved in 100 mL iPr$_2$O and 2 mL water were added. The mixture was acidified to pH=2.21 with 50% H$_2$SO$_4$ and the resulting organic phase was concentrated to half its volume (50 mL). 1 mL water was added, and the mixture was acidified again to pH=2.22 with 50% H$_2$SO$_4$. The aqueous phase was combined with the aqueous phase from the previous extraction (V=1.5 mL) and extracted with 11 mL DIPET (diisopropyl ether) after adjusting the pH to 2.17 with 5M NaOH. The combined organic phases were concentrated (V=40 mL), 1 mL water was added and the mixture was acidified to pH=2.18 with 50% H$_2$SO$_4$. The organic phase was separated and the solvent was removed in vacuo to yield a 98:2 (syn: anti) mixture of diastereomers (37.5 mL solution, assay: 28%, 76% yield).

$^1$H NMR (δ, CDCl$_3$, 300 MHz): 7.34-7.14 (m, 5H, H$_{Ar}$), 4.39-4.16 (m, 3H, COOCH$_2$ and CH(CH$_3$)), 3.58-3.31 (m, 5H, OCH$_2$CH$_3$ and CHNH), 2.69 (dd, J=7.80 Hz, J=2.37 Hz, 1H, NH), 1.47-1.12 (m, 19H, CH$_3$, CH$_2$, COCH$_2$CH$_3$ and OCH$_2$CH$_3$), 0.63 (t, J=7.00 Hz, CH$_3$). $^{13}$C NMR (δ, CDCl$_3$, 75 MHz): 169.0, 146.4, 128.0, 127.5, 126.6, 105.4, 61.0, 59.0, 57.0, 56.8, 56.3, 33.6, 24.8, 19.6, 15.3, 15.2, 14.3, 13.8.

Example 12

(R)-methyl 2,2-dimethoxy-3-(((S)-1-phenylethyl) amino)hexanoate

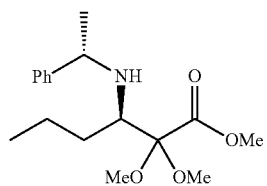 [SMILES: CCC[C@@H](N[C@@H](C)c1ccccc1)C(OC)(OC)C(=O)OC]

The compound was obtained as by-product in Example 11.

$^1$H NMR (500 MHz, CDCl$_3$): δ=7.36-7.28 (m, 4H), 7.21 (m, 1H), 3.98 (q, J=6.62 Hz, 1H), 3.74 (s, 3H), 3.24 (s, 3H), 3.11 (s, 3H), 2.85 (dd, J=8.05, 4.60 Hz, 1H), 1.70 (m, 1H), 1.49 (m, 1H), 1.37 (m, 1H), 1.31 (d, J=6.70 Hz, 3H), 1.27 (m, 1H), 0.91 (t, J=7.40 Hz, 3H).

$^{13}$C NMR (125 MHz, CDCl$_3$): δ=169.06, 145.97, 128.09, 127.33, 126.74, 104.80, 56.74, 55.69, 52.13, 50.37, 33.36, 23.74, 20.57, 14.43.

Example 13

(2S,3S)-methyl 2-((tert-butyldimethylsilyl)oxy)-3-(((S)-1-phenylethyl)amino)hexanoate (compound of Formula 13a)

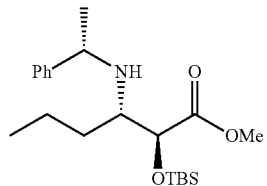 [SMILES: CCC[C@H](N[C@@H](C)c1ccccc1)[C@H](O[Si](C)(C)C(C)(C)C)C(=O)OC]

The general procedure of Example 10a was used with compounds of example 1 and 7.

$^1$H NMR (500 MHz, CDCl$_3$): δ=7.36-7.27 (m, 4H), 7.22 (m, 1H), 4.24 (d, J=2.55 Hz, 1H), 3.83 (q, J=6.42 Hz, 1H), 3.72 (s, 3H), 2.72 (m, 1H), 1.54 (m, 1H), 1.38 (m, 1H), 1.30-1.20 (m, 2H), 1.24 (d, J=6.60 Hz, 3H), 0.90 (s, 9H), 0.77 (t, J=7.70 Hz, 3H), 0.072 (s, 3H), 0.01 (s, 3H).

¹³C NMR (125 MHz, CDCl₃): δ=174.04, 146.14, 128.06, 127.03, 72.46, 57.75, 55.17, 51.51, 34.94, 25.80, 19.55, 14.04, −4.87, −5.39.

Example 14

(2S,3S)-methyl 2-(benzyloxy)-3-(((S)-1-phenylethyl) amino)hexanoate (compound of Formula 13a)

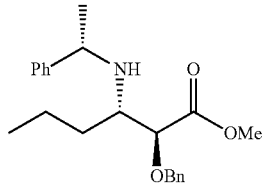 [SMILES: CCC[C@H](N[C@@H](C)c1ccccc1)[C@H](OCc1ccccc1)C(=O)OC]

General procedure of Example 10a was used with compounds of example 1 and 8.

¹H NMR (500 MHz, CDCl₃): δ=7.40-7.28 (m, 8H), 7.21 (m, 2H), 4.79 (d, J=11.95 Hz, 1H), 4.37 (d, J=12.00 Hz, 1H), 3.99 (d, J=3.15 Hz, 1H), 3.80 (q, J=6.62 Hz, 1H), 3.77 (s, 3H), 2.81 (dt, J=6.69, 2.92 Hz, 1H), 1.52 (m, 1H), 1.40 (m, 1H), 1.25 (m, 1H), 1.23 (d, J=6.60 Hz, 3H), 1.04 (m, 1H), 0.74 (t, J=7.10 Hz, 3H)

¹³C NMR (125 MHz, CDCl₃): δ=172.83, 146.03, 137.58, 128.50, 128.35, 128.22, 128.06, 127.82, 126.87, 78.17, 72.52, 56.90, 55.27, 51.70, 34.38, 24.67, 19.42, 13.91

Example 15

(S)-methyl 3-amino-2,2-dimethoxyhexanoate

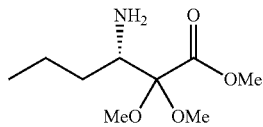

To benzylamine of Example 11 (500 mg, 1.62 mmol) in EtOAc (16 mL) was added Pd/C (170 mg, 0.16 mmol, 10% w/w) and the suspension was stirred under an H₂ atmosphere for 2.5 h. The catalyst was filtered off over celite and the solvent removed under reduced pressure to give 200 mg amine, which was used without further purification.

¹H NMR (500 MHz, CDCl₃): δ=3.80 (s, 3H), 3.31 (s, 6H), 3.06 (dd, J=10.70, 2.20 Hz, 1H), 1.65 (m, 1H), 1.57 (m, 1H), 1.40-1.30 (m, 1H), 1.01 (m, 1H), 0.92 (t, J=7.25 Hz, 3H).

¹³C NMR (125 MHz, CDCl₃): δ=168.44, 104.37, 53.76, 52.26, 50.34, 50.22, 33.46, 20.14, 14.01.

Example 16

(S)-methyl 3-((tert-butoxycarbonyl)amino)-2,2-dimethoxyhexanoate (compound of Formula 5a)

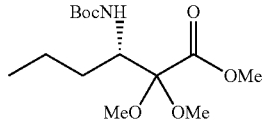 [SMILES: CCC[C@H](NC(=O)OC(C)(C)C)C(OC)(OC)C(=O)OC]

To ((S)-methyl 3-amino-2,2-dimethoxyhexanoate) of Example 15 (170 mg, 0.83 mmol) in THF (3 mL) was added Boc₂O (271 mg, 1.24 mmol) and DIPEA (432 μL, 2.48 mmol) and the mixture was stirred for 16 h. Then EtOAc was added, washed with a saturated NaHCO₃ solution, dried and concentrated.

¹H NMR (500 MHz, CDCl₃): δ=4.93 (d, J=10.05 Hz, 1H), 4.05 (dt, J=11.05, 2.20 Hz, 1H), 3.38 (s, 3H), 3.30 (s, 3H), 1.64 (m, 1H), 1.53 (s, 9H), 1.44 (m, 1H), 1.33 (m, 1H), 1.06 (m, 1H), 0.91 (t, J=7.55 Hz, 3H).

Example 17

(S)-3-((tert-butoxycarbonyl)amino)-2,2-dimethoxyhexanoic acid

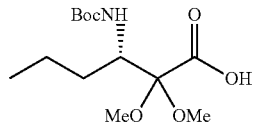 [SMILES: CCC[C@H](NC(=O)OC(C)(C)C)C(OC)(OC)C(=O)O]

To ((S)-methyl 3-((tert-butoxycarbonyl)amino)-2,2-dimethoxyhexanoate) of Example 16 (0.8 mmol) in methanol (8 mL) was added an aqueous KOH solution (0.13 mL, 2.4 mmol, 50 w/w %) and the reaction was stirred for 20 h. pH was adjusted to pH=3 with 1N HCl and extraction with CH₂Cl₂ provided 260 mg of the crude acid.

¹H NMR (500 MHz, CDCl₃): δ=4.89 (d, J=9.80 Hz, 1H), 4.07 (t, J=9.30 Hz, 1H), 3.38 (s, 3H), 3.35 (s, 3H), 1.63 (m, 1H), 1.45 (s, 9H), 1.44 (m, 1H), 1.33 (m, 1H), 1.25 (m, 1H), 0.92 (t, J=7.33 Hz, 3H).

Example 18

(S)-tert-butyl(1-(cyclopropylamino)-2,2-dimethoxy-1-oxohexan-3-yl)carbamate (compound of Formula 6a)

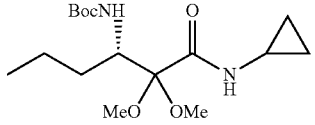 [SMILES: CCC[C@H](NC(=O)OC(C)(C)C)C(OC)(OC)C(=O)NC1CC1]

To the ((S)-3-((tert-butoxycarbonyl)amino)-2,2-dimethoxyhexanoic acid) of Example 17 (110 mg, 0.38 mmol) in CH₂Cl₂ (4 mL) was added TBTU (242 mg, 0.76 mmol) followed by cyclopropylamine (105 μL, 1.52 mmol) and the reaction was stirred for 14 h. Brine was added and the aqueous layer was extracted with CH₂Cl₂. The combined organic layers were dried and the solvent removed under reduced pressure. Column chromatography (silicagel, cyclohexane:EtOAc 3:1) gave 20 mg of amide.

¹H NMR (500 MHz, CDCl₃): δ=6.92 (bs, 1H), 5.65 (d, J=9.80 Hz, 1H), 3.97 (dt, J=10.55, 2.27 Hz, 1H), 3.27 (s, 3H), 3.18 (s, 3H), 1.44 (m, 2H), 1.43 (s, 9H), 1.31 (m, 1H), 1.12 (m, 1H), 0.89 (t, J=7.08 Hz, 3H), 0.81 (m, 2H), 0.51 (m, 2H).

$^{13}$C NMR (125 MHz, CDCl$_3$): δ=170.25, 156.72, 100.79, 78.74, 51.78, 50.58, 48.78, 32.75, 28.41, 22.03, 19.22, 14.00, 6.46, 6.41.

Example 19

Methyl 3-((tert-butoxycarbonyl)amino)-2,2-dimethoxyhexanoate (compound of Formula 5a')

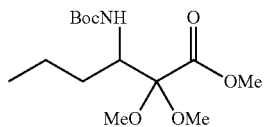 [SMILES: CCCC(NC(=O)OC(C)(C)C)C(OC)(OC)C(=O)OC]

To a solution of diisopropylamine (0.92 mL, 7.5 mmol) in THF (15 mL) at 0° C. under N$_2$ was added nBuLi (3 mL, 2.5M in hexane, 7.5 mmol) and the mixture was stirred for 20 min. The LDA was cooled to −50° C. and a solution of sulfonylamine according to Formula 10a with R$_{10}$=SO$_2$Ph (940 mg, 3 mmol) and methyl dimethoxyacetate (0.37 mL, 3 mmol) in THF (5 mL) were added. The reaction was stirred at −50° C. for 1 h, allowed to reach 0° C. over 2 h, stirred at 0° C. for 1 h and was then quenched by the addition of a saturated NH$_4$Cl solution. The layers were separated and the aqueous layer was extracted with DCM. The combined organic layers were dried and the solvent was removed under reduced pressure. Column chromatography (silicagel, hexane:EtOAc 10:1→3:1) gave 520 mg of the amino acid.

$^1$H NMR (500 MHz, CDCl$_3$): δ=4.93 (d, J=11.03 Hz, 1H), 4.05 (dt, J=10.08, 0.79 Hz, 1H), 3.81 (s, 3H), 3.38 (s, 3H), 3.30 (s, 3H), 1.63 (m, 1H), 1.45 (s, 9H), 1.42 (m, 1H), 1.34 (m, 1H), 1.03 (m, 1H), 0.91 (t, J=7.40 Hz, 3H).

Example 20

3-amino-N-cyclopropyl-2,2-dimethoxyhexanamide (compound of Formula 7a')

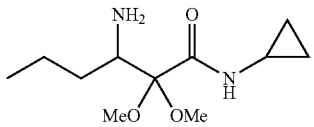 [SMILES: CCCC(N)C(OC)(OC)C(=O)NC1CC1]

To tert-butyl(1-(cyclopropylamino)-2,2-dimethoxy-1-oxohexan-3-yl)carbamate (prepared from product of Example 19 by saponification and amidation using the conditions described in example 22 and 23) (25 mg, 0.075 mmol) in DCM (1 mL) was added a catalytic amount of TFA and the mixture was stirred for 1 h. The acid was neutralized with solid NaHCO$_3$ and precipitates were filtered off. The solvent was removed under reduced pressure to give 20 mg of the amine.

$^1$H NMR (500 MHz, CDCl$_3$): δ=7.92 (bs, 2H), 7.04 (bd, J=3.78 Hz, 1H), 3.58 (m, 1H), 3.30 (s, 3H), 3.21 (s, 3H), 2.80 (m, 1H), 1.58 (m, 1H), 1.51-1.37 (m, 3H), 0.91 (t, J=6.93 Hz, 3H), 0.85 (m, 2H), 0.54 (m, 2H).

$^{13}$C NMR (125 MHz, CDCl$_3$): δ=169.17, 98.15, 53.05, 51.25, 48.98, 29.71, 22.35, 18.63, 13.52, 6.41, 6.36.

Example 21

(S)-ethyl 3-(((benzyloxy)carbonyl)amino)-2,2-diethoxyhexanoate (compound of Formula 5a)

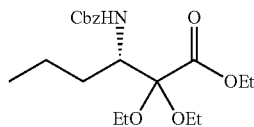 [SMILES: CCC[C@H](NC(=O)OCc1ccccc1)C(OCC)(OCC)C(=O)OCC]

To (S)-ethyl 3-amino-2,2-diethoxyhexanoate (prepared analogously to examples 1, 10, 11 and 15) (1000 mg, 4 mmol) in THF (20 mL) at ambient temperature was added K$_2$OC$_3$ (829 mg, 6 mmol), followed by CbzCl (628 μL, 4.4 mmol). After 20 h water was added and the aqueous layer was extracted with Et$_2$O. The combined organic layers were dried and the solvent was removed under reduced pressure. Column chromatography (silicagel, cyclohexane:EtOAc 10:1→5:1) gave 1000 mg of the carbamate.

$^1$H NMR (500 MHz, CDCl$_3$): δ=7.38-7.29 (m, 5H), 5.28 (d, J=10.05 Hz, 1H), 5.14 (d, J=12.60 Hz, 1H), 5.09 (d, J=12.05 Hz, 1H), 4.28-4-20 (m, 2H), 4.09 (dt, J=10.73, 2.85 Hz, 1H), 3.71 (m, 1H), 3.59 (m, 2H), 3.45 (m, 1H), 1.65 (m, 1H), 1.46-1.36 (m, 2H), 1.35-1.26 (m, 1H), 1.31 (t, J=7.10 Hz, 3H), 1.22 (t, J=7.02 Hz, 3H), 1.15 (t, J=7.20 Hz, 3H), 0.90 (t, J=7.40 Hz, 3H).

Example 22

(S)-3-(((benzyloxy)carbonyl)amino)-2,2-diethoxy-hexanoic acid

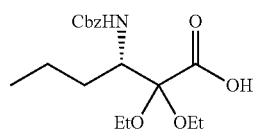 [SMILES: CCC[C@H](NC(=O)OCc1ccccc1)C(OCC)(OCC)C(=O)O]

To ethyl ester of Example 21 (1.6 g, 3.3 mmol) in ethanol (33 mL) was added an aqueous NaOH solution (6.6 mL, 1M, 6.6 mmol) and the reaction was stirred for 24 h. pH was adjusted to pH=2 with 1N HCl and extraction with CH$_2$Cl$_2$ provided 1.4 g of the crude acid.

$^1$H NMR (500 MHz, CDCl$_3$): δ=7.39-7.29 (m, 5H), 5.26 (d, J=10.40 Hz, 1H), 5.09 (d, J=12.61 Hz, 1H), 5.15 (d, J=12.30 Hz, 1H), 4.12 (bt, J=10.25 Hz, 1H), 3.64 (m, 3H), 3.42 (m, 1H), 1.63 (m, 1H), 1.45 (m, 1H), 1.33 (m, 1H), 1.28 (m, 1H), 1.27 (t, J=6.94 Hz, 3H), 1.17 (t, J=7.09 Hz, 3H), 0.91 (t, J=7.25 Hz, 3H).

$^{13}$C NMR (125 MHz, CDCl$_3$): δ=128.44, 127.97, 127.81, 101.65, 66.70, 59.65, 58.59, 52.92, 32.16, 19.25, 15.13, 14.81, 13.75.

Example 23

(S)-benzyl(1-(cyclopropylamino)-2,2-diethoxy-1-oxohexan-3-yl)carbamate (compound of Formula 6a

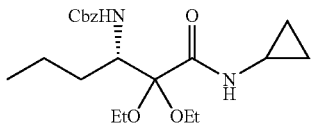 [SMILES: CCC[C@H](NC(=O)OCc1ccccc1)C(OCC)(OCC)C(=O)NC1CC1]

To the acid of Example 22 (420 mg, 1.18 mmol) in DMF (6 mL) was added HOBt (190 mg, 1.4 mmol) followed by DIC (371 μL, 2.36 mmol) and cyclopropylamine (164 μL, 2.36 mmol) and the reaction was stirred for 40 h. Brine was added and the aqueous layer was extracted with EtOAc. The combined organic layers were dried and the solvent removed under reduced pressure. Column chromatography (silicagel, cyclohexane:EtOAc 10:1→5:1→3:1) gave 330 mg of amide.

$^1$H NMR (500 MHz, CDCl$_3$): δ=7.37-7.31 (m, 4H), 7.28 (m, 1H), 6.98 (bs, 1H), 6.06 (d, J=9.50 Hz, 1H), 5.17 (d, J=12.90 Hz, 1H), 5.07 (d, J=12.60 Hz, 1H), 4.02 (dt, J=10.54, 0.41 Hz, 1H), 3.60 (m, 1H), 3.53 (m, 1H), 3.44 (m, 1H), 3.31 (m, 1H), 2.71 (m, 1H), 1.61 (bs, 1H), 1.45 (m, 2H), 1.32 (m, 1H), 1.21 (t, J=7.10 Hz, 3H), 1.19 (m, 1H), 1.12 (t, J=6.92 Hz, 3H), 0.89 (t, J=7.08 Hz, 3H), 0.81 (m, 2H), 0.51 (m, 2H) $^{13}$C NMR (125 MHz, CDCl$_3$): δ=170.72, 157.46, 137.20, 128.29, 127.62, 127.50, 100.28, 66.16, 58.77, 56.80, 53.33, 32.44, 21.98, 19.24, 15.34, 14.93, 13.91, 6.44

Example 24a (S)-3-amino-N-cyclopropyl-2,2-diethoxyhexanamide, (compound of Formula 7a)

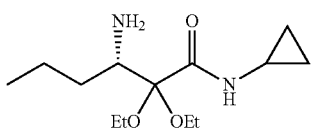 [SMILES: CCC[C@H](N)C(OCC)(OCC)C(=O)NC1CC1]

To a suspension of carbamate of Example 23 (300 mg, 0.76 mmol) in EtOAc (4 mL) was added Pd/C (85 mg, 0.08 mmol, 10% w/w) and the suspension was stirred under an H$_2$ atmosphere for 1.5 h. The catalyst was filtered through a pad of celite and the solvent was removed under reduced pressure to give 210 mg amine, which was used without further purification.

$^1$H NMR (500 MHz, CDCl$_3$): δ=6.99 (bs, 1H), 3.56-3.40 (m, 4H), 2.97 (bd, J=10.72 Hz, 1H), 2.73 (m, 1H), 1.79 (bs, 2H, NH$_2$, pH-dependent), 1.59 (m, 1H), 1.48 (m, 1H), 1.33 (m, 1H), 1.20 (t, J=7.09 Hz, 6H), 1.09 (m, 1H), 0.90 (t, J=7.25 Hz, 3H), 0.79 (m, 2H), 0.50 (m, 2H).

$^{13}$C NMR (125 MHz, CDCl$_3$): δ=170.07, 58.61, 56.92, 54.47, 33.02, 22.04, 20.06, 15.45, 15.16, 14.06, 6.50.

Example 24b

Protecting Group Exchange as One-Pot Procedure

Preparation of (S)-3-(tert-butoxycarbonylamino)-2,2-diethoxyhexanoic acid by protecting group exchange of Ethyl (S)-2,2-diethoxy-3-((S)-1-phenylethylamino)hexanoate and saponification of Ethyl(S)-3-(tert-butoxycarbonylamino)-2,2-diethoxyhexanoate:

FIG. 2 shows the reaction scheme of this reaction.

Step 1—preparation of Ethyl(S)-3-(tert-butoxycarbonylamino)-2,2-diethoxyhexanoate: BOC$_2$O (9.19 g, 42.1 mmol) was added to a solution of Ethyl(S)-2,2-diethoxy-3-((S)-1-phenylethylamino)hexanoate (8.1 g, 23 mmol) in 500 mL EtOH. The flask was flushed with nitrogen and a slurry of Pd/C (10 mol %, 10% w/w) in EtOH was added. Forming gas (95% N$_2$, 5% H$_2$) was bubbled through the mixture for 23 hours at room temperature, after which the catalyst was filtered over a pressure strainer and washed with 20 mL EtOH. The solvent was removed in vacuo to give 9.9 g crude Ethyl (S)-3-(tert-butoxycarbonylamino)-2,2-diethoxyhexanoate, which was used without further purification in the next step.

$^1$H NMR (δ, CDCl$_3$, 300 MHz): 4.98 (d, J=10.50 Hz, NH), 4.28-4.17 (m, 2H, COOCH$_2$CH$_3$), 4.00-3.95 (dt, J=10.50 and 2.50 Hz, CHNH), 3.72-3.40 (m, 4H, OCH$_2$CH$_3$), 1.41-1.14 (m, 22H, BOC—CH$_3$, COCH$_2$CH$_3$ and OCH$_2$CH$_3$), 0.88 (t, J=7.25 Hz, CH$_3$). $^{13}$C NMR (δ, CDCl$_3$, 75 MHz): 168.9, 156.0, 146.7, 102.0, 85.1, 78.9, 61.4, 58.7, 58.6, 53.1, 33.3, 28.4, 27.4, 19.4, 15.3, 15.0, 14.2, 13.9.

Step 2—preparation of (S)-3-(tert-butoxycarbonylamino)-2,2-dimethoxyhexanoic acid: A solution of KOH (6.95 g, 123.9 mmol) in 100 mL water was added to a solution of Ethyl(S)-3-(tert-butoxycarbonylamino)-2,2-diethoxyhexanoate (8.6 g, 24.6 mmol) in 100 mL EtOH. Further 100 mL EtOH were added to obtain a clear solution and the mixture was stirred at room temperature for 23 hours. Dichloromethane (200 mL) and water (200 mL) were added, and the pH of the mixture was adjusted with conc. HCl from 12.5 to 2.5. The phases were separated, and the aqueous phase was extracted twice with dichloromethane (100 mL). The combined organic phases were dried over Na$_2$SO$_4$ and the solvent was removed in vacuo to yield 6.3 g (S)-3-(tert-butoxycarbonylamino)-2,2-diethoxyhexanoic acid (80% yield).

$^1$H NMR (δ, CDCl$_3$, 300 MHz): 9.13 (bs, 1H, COOH), 5.00 (d, J=10.00 Hz, NH), 4.02 (t, J=10.00 CHNH), 3.70-3.39 (m, 4H, OCH$_2$CH$_3$), 1.63-1.12 (m, 19H, BOC—CH$_3$ and OCH$_2$CH$_3$), 0.89 (t, J=7.25 Hz, CH$_3$). $^{13}$C NMR (δ, CDCl$_3$, 75 MHz): 169.7, 156.4, 101.8, 79.3, 59.2, 58.6, 52.3, 32.4, 28.3, 26.9, 19.4, 14.9, 14.4, 13.8.

Preparation of (S)-tert-butyl 1-(cyclopropylamino)-2,2-diethoxy-1-oxohexan-3-ylcarbamate by amidation of (S)-3-(tert-butoxycarbonylamino)-2,2-diethoxyhexanoic acid FIG. 3 shows the reaction scheme of this reaction.

(S)-3-(tert-butoxycarbonylamino)-2,2-diethoxyhexanoic acid (8.03 g, 25.1 mmol) was dissolved under nitrogen in 400 mL DMF and HOBt (4.10 g, 30.3 mmol), DIC (7.7 mL, 49.7 mmol) and cyclopropylamine (3.5 mL, 50.0 mmol) were added to the reaction mixture. After stirring for 24 hours at room temperature, the mixture was quenched with 400 mL 5% NaCl and 800 mL EtOAc and the phases were separated. The aqueous phase was extracted with 100 mL EtOAc, the combined organic phases were dried over Na$_2$SO$_4$ and the solvent was removed in vacuo. Purification by column chromatography on silica gel (CHX:EE 10:1→3:1) yielded 3.2 g (S)-tert-butyl 1-(cyclopropylamino)-2,2-diethoxy-1-oxohexan-3-ylcarbamate.

$^1$H NMR (δ, CDCl$_3$, 300 MHz): 6.96 (bs, 1H, CONH), 5.70 (d, J=9.78 Hz, 1H, NH), 3.91 (t, J=10.55 Hz, CHNH), 3.63-3.26 (m, 4H, OCH$_2$CH$_3$), 2.68 (m, 1H, CH(CH$_2$)$_2$), 1.41 (s, 11H, BOC—CH$_3$ and CH$_2$), 1.21-1.12 (m, 8H, OCH$_2$CH$_3$ and CH$_2$), 0.88 (t, J=7.06 Hz, 3H, CH$_3$), 0.81-0.78 (m, 2H, CH$_2$), 0.53-0.48 (m, 2H, CH$_2$). $^{13}$C NMR (δ, CDCl$_3$, 75 MHz): 170.8, 157.0, 100.5, 78.5, 58.6, 56.8, 52.6, 32.5, 28.4, 22.0, 19.3, 15.4, 15.0, 14.0, 6.5, 6.4.

Deprotection of (S)-tert-butyl 1-(cyclopropylamino)-2,2-diethoxy-1-oxohexan-3-ylcarbamate (see FIG. 4)

TFA (2.45 mL, 32.1 mmol) was added to a solution of (S)-tert-butyl 1-(cyclopropylamino)-2,2-diethoxy-1-oxohexan-3-ylcarbamate (2.3 g, 6.41 mmol) in 45 mL CH$_2$Cl$_2$ and the mixture was stirred at room temperature for 18 hours. A saturated NaHCO$_3$ solution was carefully added to the mixture, the aqueous phase was extracted with CH$_2$Cl$_2$ (2×30 mL) and the combined organic phases were dried over Na$_2$SO$_4$. Removal of the solvent in vacuo yielded 1.44 g (3S)-3-Amino-N-cyclopropyl-2,2-diethoxyhexanamide as a pale yellow oil.

$^1$H NMR (δ, CDCl$_3$, 300 MHz): 7.01 (bs, 1H, CONN), 3.61-3.39 (m, 4H, OCH$_2$CH$_3$), 3.08 (dd, J=10.56 Hz, J=2.64 Hz, 1H, CHNH$_2$), 2.79-2.70 (m, 3H, CH(CH$_2$)$_2$ and NH$_2$ (pH-dependent)), 1.64-1.31 (m, 4H, CH$_2$), 1.22 (t, J=7.04 Hz, 6H, OCH$_2$OH$_3$), 0.92 (t, J=7.14 Hz, 3H, CH$_3$), 0.85-0.78 (m, 2H, CH$_2$), 0.55-0.52 (m, 2H, CH$_2$). $^{13}$C NMR (δ, CDCl$_3$, 75 MHz): 170.0 (CONH), 101.5 (C(OEt)$_2$), 58.7 (OCH$_2$CH$_3$), 57.0 (OCH$_2$CH$_3$), 54.4 (CHNH$_2$), 32.7 ((CH$_2$)$_2$CH$_3$), 22.0 (CH(CH$_2$)$_2$), 19.9 ((CH$_2$)$_2$CH$_3$), 15.4 (OCH$_2$CH$_3$), 15.1 (OCH$_2$CH$_3$), 14.0 ((CH$_2$)$_2$CH$_3$), 6.5 (CH(CH$_2$)$_2$), 6.5 (CH(CH$_2$)$_2$).

Example 25

Diethoxy-Telaprevir (Compound of Formula 9a)

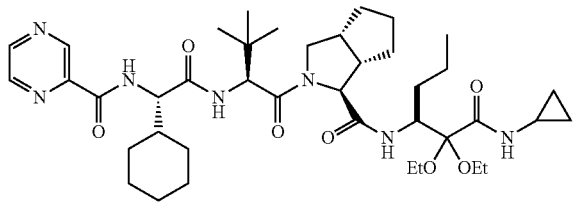 [SMILES: CCC[C@H](NC(=O)[C@@H]1[C@H]2CCC[C@H]2CN1C(=O)[C@@H](NC(=O)[C@@H](NC(=O)c1cnccn1)C1CCCCC1)C(C)(C)C)C(OCC)(OCC)C(=O)NC1CC1]

DCM as Solvent

To a solution of the compound of Formula 8a (362 mg, 0.704 mmol), EDC.HCl (162 mg, 0.844 mmol) and HOBt (119 mg, 0.844 mmol) in DCM (10 mL) was added amine of Example 24 (200 mg, 0.774 mmol) and the mixture was stirred at ambient temperature for 15 h. Water was added and the layers were separated. The aqueous layer was extracted with DCM. The combined organic layers were washed with an aqueous, saturated NaHCO$_3$ solution and brine, dried over Na$_2$SO$_4$ and the organic solvent was removed under reduced pressure to give 570 mg diethoxy-telaprevir.

DMF as Solvent 2.9 g of amine of example 24 (10.74 mmol, 1.2 eq) were dissolved in 30 ml DMF. To the mixture 4.6 g of compound 8a (8.95 mmol, 1.0 eq), 3.43 g EDC.HCl (17.9 mmol, 2.0 eq) and 2.5 ml triethylamine (17.9 mmol, 2 eq) and 1.7 g HOBt*H$_2$O (10.74 mmol, 1.2 eq) was added. The mixture was stirred for 3.5 until no starting material was detected. To the reaction mixture 90 ml ethyl acetate and 50 ml water was added. pH was adjusted to 1.5 by addition of 2M HCl. The organic phase was separated and the aqueous phase was washed with 50 ml ethyl acetate. The combined organic phases were washed with saturated sodium bicarbonat and the aqueous phase was washed with 30 ml ethyl acetate. The combined organic phases were washed with 50 ml water and the solvent was removed to dryness. The yellow residue was dissolved in methylene chloride and the solvent was again removed to dryness. 6.5 g of a white solid was isolated (96% yield).

$^1$H NMR (500 MHz, CDCl$_3$): δ=9.38 (d, J=1.26 Hz, 1H), 8.74 (d, J=2.52 Hz, 1H), 8.55 (dd, J=2.30, 1.48 Hz, 1H), 8.36 (d, J=9.46 Hz, 1H), 7.11 (d, J=9.46 Hz, 1H), 6.99 (d, J=2.83 Hz, 1H), 6.47 (d, J=9.46 Hz, 1H), 4.70 (d, J=9.77 Hz, 1H), 4.46 (dd, J=8.88, 6.55 Hz, 1H), 4.33 (d, J=10.25 Hz, 1H), 4.21 (d, J=4.10 Hz, 1H), 3.88 (dd, J=10.40, 7.25 Hz, 1H), 3.72 (dd, J=10.25, 2.68 Hz, 1H), 3.60 (m, 1H), 3.53 (m, 1H), 3.41 (m, 1H), 3.30 (m, 1H), 2.85 (m, 1H), 2.76 (m, 1H), 2.72 (m, 1H), 1.96-1.82 (m, 3H), 1.76-1.60 (m, 7H), 1.57 (bs, 6H), 1.45-1.35 (m, 3H), 1.33-1.22 (m, 2H), 1.20 (t, J=6.93 Hz, 3H), 1.12 (t, J=7.09 Hz, 3H), 1.08 (m, 2H), 1.01 (s, 9H), 0.86 (t, J=7.25 Hz, 3H), 0.83 (m, 2H), 0.53 (m, 2H).

1H-NMR (500 MHz): d6-DMSO
δ=9.18 (1H, d, J=1.5 Hz); 8.89 (1H, d, J=2.5 Hz); 8.75 (1H, dd, J$_2$=2.5 Hz, J=1.6 Hz); 8.50 (1H, d, J=9.2 Hz); 8.22 (1H, d, J=9.2 Hz); 7.61 (1H, d, J=4.1 Hz); 7.34 (1H, d, J=9.6 Hz); 4.67 (1H, dd, J=9.1 Hz, J$_7$=6.4 Hz); 4.54 (1H, d, J=9.3 Hz); 4.17 (1H, d, J=3.8 Hz); 4.12 (m, 1H); 3.73-3.63 (2H, m); 3.51-3.19 (4H, m); 2.63 (2H, m); 2.57 (1H, m); 1.81-0.99 (21H, m); 1.13 (3H, t, J=7.0 Hz); 1.06 (3H, t, J=7.1 Hz); 0.93 (9H, s); 0.79 (3H, t, J=7.2 Hz); 0.63-0.47 (4H, m). 13C-NMR (125 MHz): d6-DMSO
δ=171.2, 170.3, 169.2, 169.0, 161.9, 147.8, 144.0, 143.4, 143.3, 100.3, 65.4, 57.4, 57.0, 56.4, 56.3, 54.1, 50.3, 46.9, 42.5, 41.3, 34.4, 31.9, 31.7, 29.1, 27.9, 25.7, 25.6, 25.5, 25.0, 24.7, 26.3, 22.2, 15.1, 15.0, 13.6, 5.7, 5.6.

Example 26

Telaprevir (Compound of Formula 1)

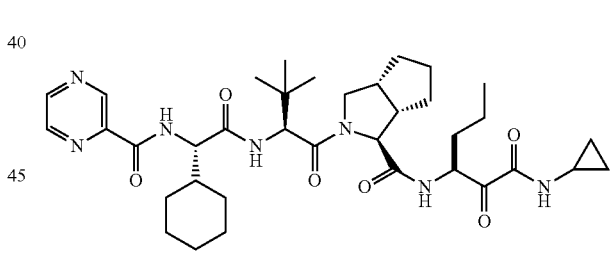

TFA Deprotection:
To a compound of formula 9a of Example 25 (20 mg, 0.026 mmol) was added TFA (900 μL), acetone (100 μL) and water (10 μL). After 22 h, full conversion to telaprevir occurred.

HCl-Deprotection:
To a solution of 5.0 g (6.63 mmol) diethoxy-telaprevir (compound of formula 9a) in 10 ml acetone 45 ml conc. aqueous HCl was added and stirred for 5.5 h until complete conversion was observed. No oxidative byproduct (IMP 1) at rt=3.0 min was detected. Afterwards 150 ml water and 75 ml methylene chloride was added. pH 5 2.5 was adjusted by slow addition of 5M aqueous NaOH. The organic phase was removed and the aqueous phase was extracted with 75 ml methylene chloride. The organic phases were combined and the organic solvent was removed to dryness. 4.3 g of yellow foam was isolated. IPC HPLC shows no oxidative byproduct (IMP 1) at rt=3.0 min. After crystallization from 15 ml iso-propanol 3.4 g telaprevir was isolated.

IPC HPLC:
Column: Water X-Bridge, Phenyl, 4.6×50 mm, 2.5 μm
Temp: 60° C. Flow: 1 ml/min
Detection: 270 nm
Eluent A: 0.77 g Ammonium acetate/100 ml MeOH/900 ml $H_2O$
Eluent B: 0.77 mg Ammonium acetate/900 ml MeOH/100 ml $H_2O$
Gradient: 0 min: 50% B, 15 min: 95% B, 17 min: 95% B, 18 min: 50% B
$H_2SO_4$-deprotection:
100 mg diethoxy-telaprevir was dissolved in 100 μl acetone, 0.5 ml water and 0.5 ml conc. $H_2SO_4$ at 0° C. The mixture was stirred at room temperature for 17 h until complete conversion was observed. Water and methylene chloride was added, the organic phase was separated and solvent was reduced to dryness.

Example 27

Telaprevir (Compound of Formula 1) Obtained Via Oxidation

Figure 5:
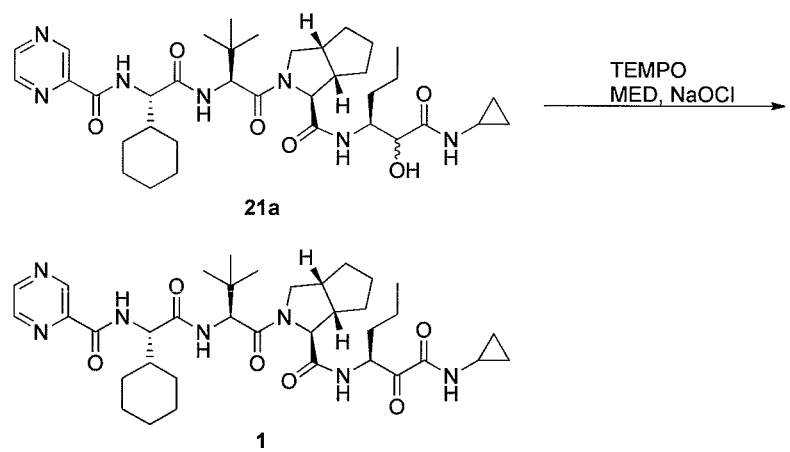
FIG. 5: Shows the preparation of telaprevir via oxidation of hydroxyl-telaprevir as last step.

As demonstrated below, the preparation of telaprevir via oxidation of hydroxyl-telaprevir as last step (aspects 5 to 7 described herein) results in the formation of impurities (see FIG. 5 for the reaction scheme):

To a solution of 28.1 g hydroxyl-telaprevir in 230 ml methylene chloride 3.5 ml 15% aqueous KOH, 13 ml 7.5% aqueous $NaHCO_3$ was added and 170.3 mg (2.7 mol %) TEMPO was added. To the stirred mixture 43 ml 6-14% NaOCl solution was added. After 19.5 h, 86% conversion was observed. Additional 7 ml NaOCl was added and after an additional hour complete conversion was observed. IPC HPLC shows 2-3 area % of oxidative byproduct with rt=3 min. 150 ml water was added, the organic phase was separated and the aqueous phase was extracted with methylene chloride. The combined organic phases were washed with 150 ml 1% $Na_2S_2O_3$ and the aqueous phase was extracted with 75 ml methylene chloride. The combined organic phases were extracted with 100 ml water and the aqueous phase was extracted with 75 ml methylene chloride. The organic phases were combined and solvent was removed to dryness leading to 27.0 g of yellow foam containing about 1.5 area % of oxidative byproduct (IMP1) with rt=3.0 min. After crystallization from 100 ml isopropanol, 20.3 g telaprevir was isolated containing 0.98 area % of oxidative byproduct (IMP1) with rt=3.0 min and 0.11 area % of a second oxidative byproduct (IMP2).

HPLC Analysis
Column: XBridge C18; 4.6×150 mm, 3.5 μm;
Stock solution 1: Dissolve 0.9 g of $K_2HPO_4$ in 1000 mL of water
Stock solution 2: Mix 500 mL of MeOH, 150 mL of EtOH and 350 mL of ISO
Eluent A: Mix 400 mL of stock solution 1 with 100 mL of stock solution 2
Eluent B: Mix 100 mL of stock solution 2 with 400 mL of ACNL
Solvent: Mix 400 mL of EtOH, 100 mL of water and 100 μL of $H_3PO_4$
Flow rate: 1.1 mL/min
Oven temperature: 38° C.
Stop time: 35 min (Post-time 6 min)
Injection volume: 6.0 μL
Detection: 210 nm
Gradient:

| t (min) | 0 | 8 | 25 | 26 | 35 |
|---|---|---|---|---|---|
| % B | 10 | 35 | 80 | 95 | Stop |

Structure of IMP2 (LC-MS: 582.4):

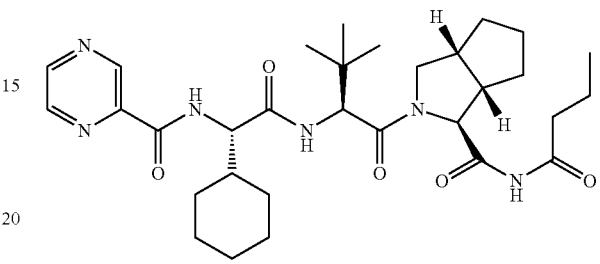

Isolation of Oxidative Byproduct (IMP1) with Rt=3.0 min:
From a mother liquor of crystallization of telaprevir according example above containing IMP1 the solvent was removed to dryness leading to 9.0 g of yellow foam. The foam was dissolved in 10 ml methylene chloride and 100 ml water was added. pH was adjusted to 12.5. IMP1 was then found in the aqueous phase. The phases were separated and to the aqueous phase 100 ml methylene chloride was added. Afterwards pH was adjusted to 2.5 and the organic phase was separated. The organic solvent was removed to dryness and 0.8 g of yellow foam was isolated.

$^1$H NMR (300 MHz, $CDCl_3$): δ=9.44 (m, 1H), 8.75 (m, 1H), 8.56 (s, 1H), 8.37 (m, 1H), 7.53 (d, 1H), 4.84 (d, 1H), 4.72 (m, 1H), 4.59 (m, 2H), 3.81 (m, 3H), 2.78-3.00 (m, 2H), 0.86-2.00 (m, 33H).
LC-MS: 612.3 u
Structure of IMP 1:

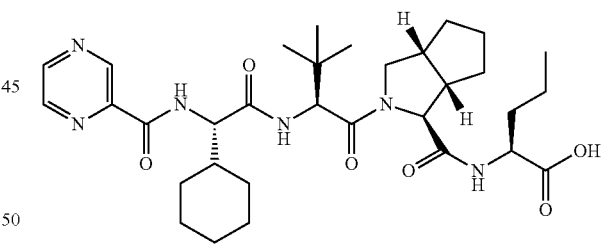

Example 28

Impurities Contained in Commercially Available Telaprevir Product

Analysis of commercially available telaprevir tablet in solution:
One Incivo® FCT (film coated tablet) tablet containing 375 mg telaprevir was treated with 20 ml water until the tablet file was destroyed. To the suspension a 60/40 acetonitrile/water mixture was added until a volume of 1 L was reached. Solid residues were removed and the solution was analyzed via HPLC analysis: 1.6 area % of IMP2 and 0.66 area % of an stereoisomer of telaprevir were found.

Analysis of Isolated API of Commercially Available Telaprevir Tablets:

9 Incivo® FCT tablets (containing in total 3.375 g telaprevir) were treated with 200 ml water. After 10 min 200 ml methylene chloride was added to achieve a suspension. The solid was removed via filtration and the filter cake was washed with methylene chloride. To the biphasic mixture NaCl was added. The phases were separated (aqueous phase only contains very small amounts of telaprevir) and the organic phase was filtered again and again washed with brine and water. After phase separation, the organic solvent was removed to dryness and the residue was again dissolved in methylene chloride and again the solvent was removed to dryness: 3.0 g of blue foam was isolated. 0.14 area % of IMP1 and 1.1 area % of IMP2 was found.

A further sample prepared according to the procedure described above (example 27) was subjected to LC-MS analysis wherein an impurity with molecular mass of 695.4 (telaprevir+16) was found. Three possible structural options are given below.

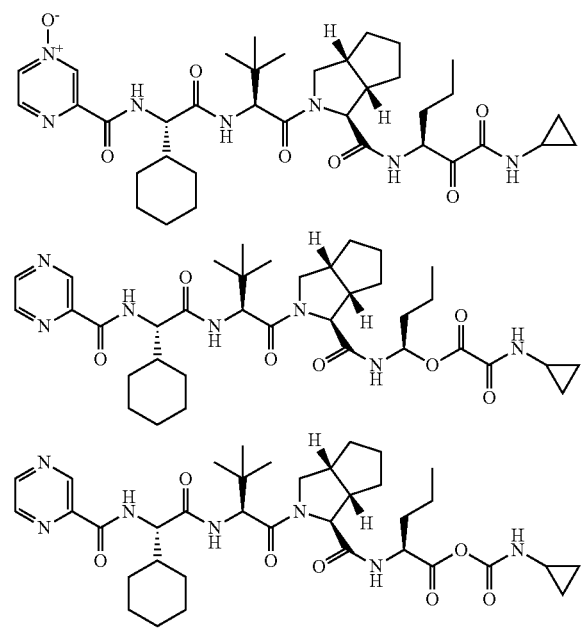

Figure 6:
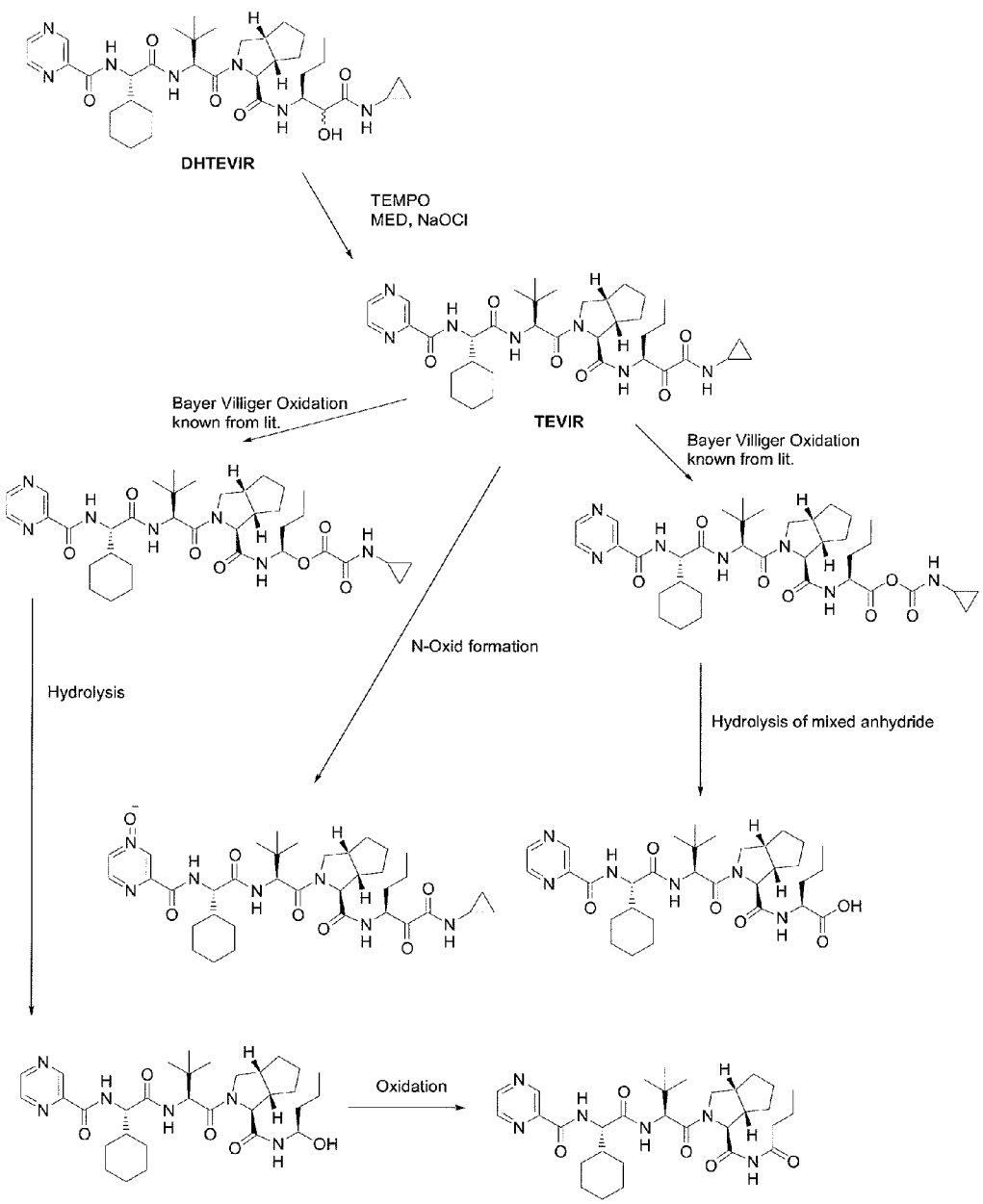
FIG. 6: Shows possible mechanisms which result in the formation of oxidative byproducts.

A possible mechanism for the formation of described oxidative byproducts is described in FIG. 6.

Example 27

Cyclobutylacetonitrile

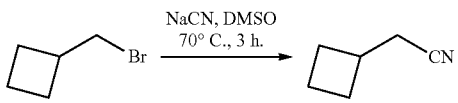 [SMILES: BrCC1CCC1 ; N#CCC1CCC1]

Bromomethylcyclobutane (29.30 g, 0.2 mol) was added dropwise to a suspension of sodium cyanide (14.65 g, 0.3 mol) in 230 mL DMSO at 60° C., whereupon the temperature of the reaction increased to 75° C. The mixture was stirred at 70° C. for three hours, cooled to room temperature and carefully poured onto 1200 mL crushed ice. The mixture was stirred for 30 minutes and extracted with diethyl ether (3×400 mL). The combined organic phases were washed with 6N HCl (400 mL), sat. NaHCO$_3$ (400 mL) and sat. NaCl (400 mL), dried over Na$_2$SO$_4$ and the solvent was evaporated to yield 16.37 g of cyclobutylacetonitrile (88%). $^1$H NMR (300 MHz, CDCl$_3$): 2.61 (m, 1H, CH), 2.39 (d, J=6.69 Hz, 2H, CH$_2$CN), 2.18-2.10 (m, 2H, CH$_2$), 1.95-1.73 (m, 4H, CH$_2$).

Example 28

Cyclobutylacetaldehyde

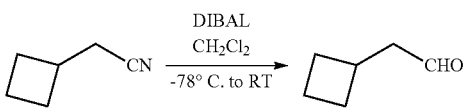 [SMILES: N#CCC1CCC1 ; O=CCC1CCC1]

Cyclobutylacetonitrile (16.37 g, 0.17 mol) was suspended in 132 mL CH$_2$Cl$_2$ and cooled to −78° C. DIBAL (1M solution in CH$_2$Cl$_2$, 185 mL, 0.19 mol) was added dropwise and the mixture was stirred at −78° C. for one hour, warmed to 0° C. and stirred at this temperature for two hours. The mixture was then cooled to −20° C., carefully quenched with ~400 mL NH$_4$Cl and stirred at −10° C. for 30 minutes. 1N HCl was added to acidify the mixture (pH=1-2), the aqueous phase was extracted with CH$_2$Cl$_2$ (3×300 mL) and the combined organic phases were washed with sat. NaCl (300 mL). Due to its low boiling point, cyclobutylacetaldehyde was used in the next reaction as a solution in CH$_2$Cl$_2$ assuming a 70% yield.

Example 29

N-(2-cyclobutylethylidene)-1-phenylmethanamine

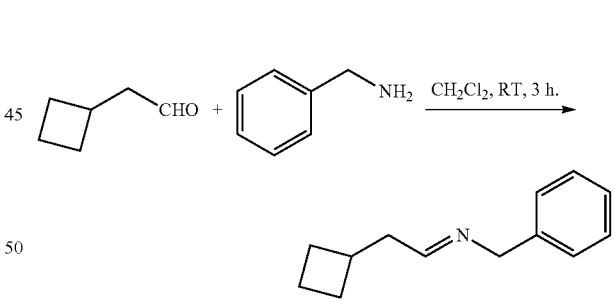

Benzylamine (2.95 g, 27.5 mmol) was added to a mixture of cyclobutylacetaldehyde (30.6 mmol) in CH$_2$Cl$_2$ (~238 mL) and molecular sieves (5.0 g) and the mixture was stirred at room temperature for 5.5 hours. The mixture was filtered over Celite and the solvent was removed under vacuum to yield 5.45 g of crude N-(2-cyclobutylethylidene)-1-phenylmethanamine.

$^1$H NMR (300 MHz, CDCl$_3$): 7.73 (1H, N=CH), 7.34-7.26 (m, 5H, Ph), 4.58 (s, 2H, NCH$_2$), 2.62 (m, 1H, CH(CH$_2$)$_3$), 2.45 (s, 1H, N=CHCH$_2$), 2.13-1.74 (m, 6H, CH(CH$_2$)$_3$). $^{13}$C NMR (75 MHz, CDCl$_3$): 164.9 (N=CH), 139.4, 128.4, 127.8, 126.9 (Ph), 65.2 (NCH$_2$), 42.9 (CH(CH$_2$)$_3$), 33.0 (N=CHCH$_2$), 28.1, 18.8 (CH(CH$_2$)$_3$).

Example 30

Ethyl 3-(benzylamino)-4-cyclobutyl-2,2-diethoxybutanoate (compound of formula 4b')

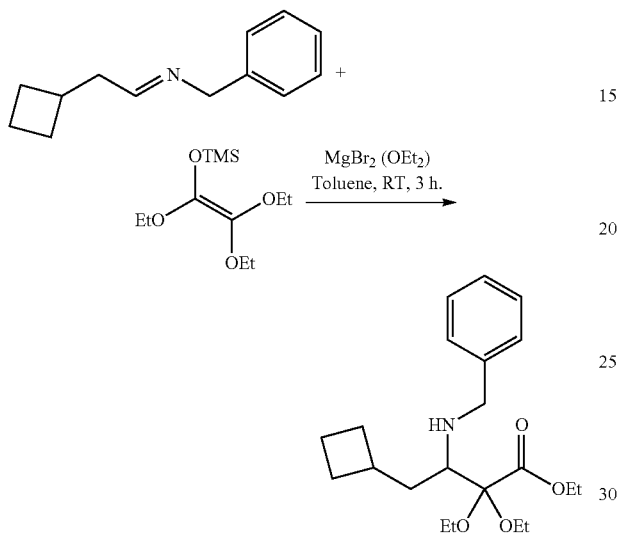

N-(2-cyclobutylethylidene)-1-phenylmethanamine (1.00 g, 5.3 mmol) was dissolved in 23 mL toluene, MgBr$_2$.OEt$_2$ (2.07 g, 8.0 mmol) was added and the mixture was stirred at room temperature for 15 minutes. Trimethyl(1,2,2-triethoxyvinyloxy)silane (1.83 g, 7.4 mmol) was added, and the mixture was stirred at room temperature. After 3 hours, the reaction was quenched with water (30 mL) and acidified to pH=2 with hydrochloric acid. The organic phase was washed with sat. NaHCO$_3$, dried over Na$_2$SO$_4$ and the solvent was removed under vacuum to yield the crude product. Column chromatography (silica, cyclohexane:ethyl acetate 10:1) yielded 1.1 g ethyl 3-(benzylamino)-4-cyclobutyl-2,2-diethoxybutanoate.

$^1$H NMR (300 MHz, CDCl$_3$): 7.31-7.18 (m, 5H, Ph), 4.26-4.15 (m, 2H, COOCH$_2$CH$_3$), 3.96 (d, J=12.8 Hz, PhCH$_2$), 3.77 (d, J=12.8 Hz, PhCH$_2$), 3.71-3.42 (m, 5H, OCH$_2$CH$_3$ and NHCH), 2.79 (dd, J=2.7 Hz, J=10.1 Hz, NH), 2.43 (m, 1H, CH(CH$_2$)$_3$), 1.99-1.54 (m, 7H, CH(CH$_2$)$_3$ and NHCHCH$_2$), 1.32-1.16 (m, 10H, COOCH$_2$CH$_3$, OCH$_2$CH$_3$ and NHCHCH$_2$). $^{13}$C NMR (75 MHz, CDCl$_3$): 167.7 (CO), 140.2 (Ph$^{ipso}$), 127.3 (Ph$^m$), 127.0 (Ph$^o$), 125.5 (Ph$^p$), 103.4 (C(OEt)$_2$), 60.0 (COOCH$_2$CH$_3$), 57.7 (OCH$_2$CH$_3$), 57.2 (NHCH), 56.6 (OCH$_2$CH$_3$), 52.6 (PhCH$_2$), 37.3 (NH-CHCH$_2$), 32.3 (CH(CH$_2$)$_3$), 27.5, 27.0, 17.3 (CH(CH$_2$)$_3$), 14.2 (OCH$_2$CH$_3$), 13.1 (COOCH$_2$CH$_3$).

CITED LITERATURE

WO 2007/022459 A2;
WO 2007/109023 A1;
WO 2007/138928 A1;
WO 2009/114633 A1;
WO 2009/152474 A2;

Gizecki et al. "Diastereoselective preparation of novel tetrahydrooxazinones via heterocycloaddition of N-Boc, O-Me-acetals", Tetrahedron Letters, 2004, 45, 9589-9592;
Han, S.-Y.; Kim, Y.-A. Tetrahedron 2004, 60, 2447-2467;
B. Pelotier et al. "The Formation of Silylated β-Lactams from Silylketenes through Lewis Acid Promoted [2+2] Cycloaddition: A Combined Theoretical and Experimental Study" Eur. J. Org. Chem. 2005, 2599-2606;
"March's advanced organic chemistry" Ed. 5. p. 1185-1187;
T. W. Greene & P. G. M Wuts, "Protective Groups in Organic Synthesis," 4th Edition, John Wiley & Sons, Inc. (2007), particularly relevant pages: p 189-196 (synthesis of ROTBS); p 102-120 (synthesis of ROBn); p 553-561 (synthesis of RCO2Me); p 814-818 (synthesis of NH-Bn); p 748-756 (synthesis of NHCbz); p 725-735 (synthesis of NHBoc).
Yamamoto "Highly Selective and Operationally Simple Synthesis of Enantiomerically Pure β-Amino Esters via Double Stereodifferentiation" Journal of the American Chemical Society 1993, 115, 1151;
Yamamoto "Practical Preparation of α-Hydroxy-β-Amino Ester Units; Stereoselective Synthesis of Taxol Side Chain and Norstatine" Tetrahedron 1994, 50, 9, 2785.
Yin et al. "Recent Applications of α-Amido Sulfones as in situ Equivalents of Activated Imines for Asymmetric Catalytic Nucleophilic Addition Reactions" Synthesis, 2010, 21, 3583-3595.

The invention claimed is:

1. Process for the preparation of telaprevir of Formula 1

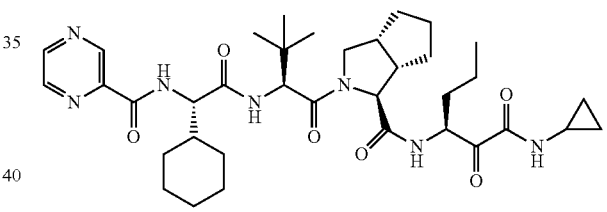

or boceprevir according to Formula 25

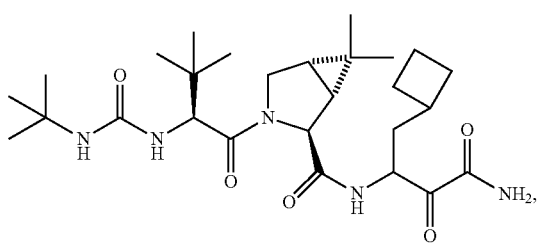

or a pharmaceutically acceptable salt or solvate thereof, comprising the steps of:

i) providing a compound of Formula 2a or 2b

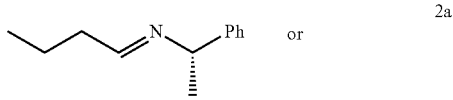

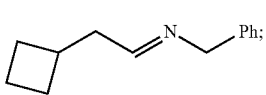

2b ii) bringing the compound of Formula 2a or 2b into contact with a compound of Formula 3

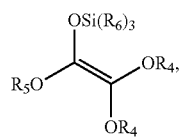

3 wherein R₄ and R₅ are independently methyl or ethyl; and R₆ is methyl or ethyl in the presence of an acid, thereby obtaining a compound of Formula 4a or 4b'

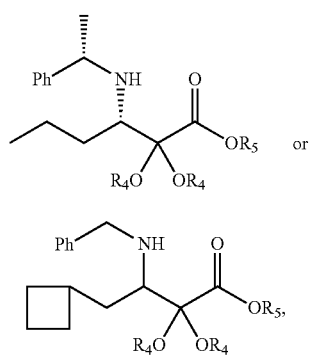

4a

4b' wherein R₄ and R₅ are as defined above, wherein optionally the stereochemical purity of the compound of Formula 4a is improved by extraction of said compound from the reaction mixture;

iii) conducting the steps of (a) deprotecting the compound of Formula 4a or 4b' in order to provide a NH₂-group and (b) protecting the obtained NH₂-group, either separately or as a one-pot process, in order to provide a compound of Formula 5a or 5b'

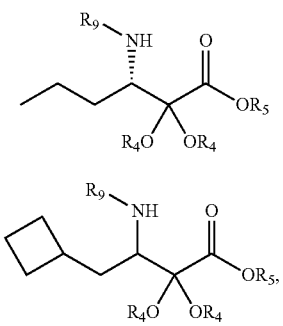

5a

5b' wherein R₄ and R₅ are as defined above; and R₉ is a protective group;

iv) conducting the steps of (a) hydrolyzing the compound of Formula 5a or 5b' in order to substitute the OR₅-group with an OH-group and (b) performing an amine coupling reaction of the compound of Formula 5a with said OH-group with cyclopropylamine in the presence of one or more coupling agents in order to provide a compound of Formula 6a or reacting the compound of Formula 5b' with said OH-group with an ammonia source in the presence of one or more coupling agents in order to provide a compound of Formula 6b'

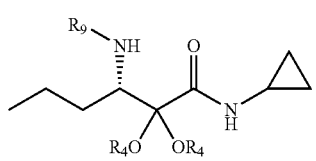

6a

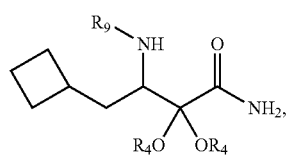

6b' wherein R₄ and R₉ are as defined above;

v) deprotecting the compound of Formula 6a or 6b' in order to provide a compound of Formula 7a or 7b',

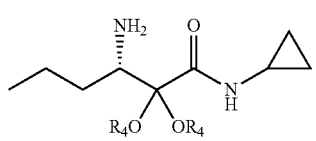

7a

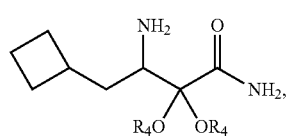

7b' wherein R₄ is as defined above;

vi) bringing the compound of Formula 7a into contact with a compound of Formula 8a or bringing the compound of Formula 7b' into contact with compound of Formula 8b

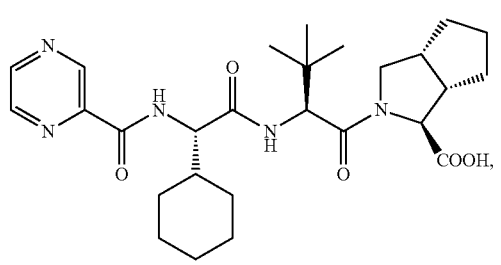

8a

-continued

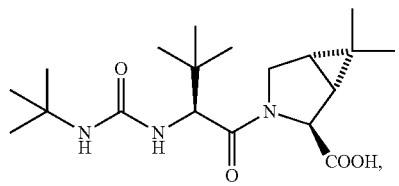
8b in the presence of one or more coupling agents, thereby obtaining a compound of Formula 9a or 9b',

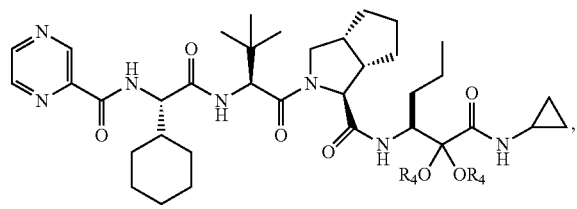
9a

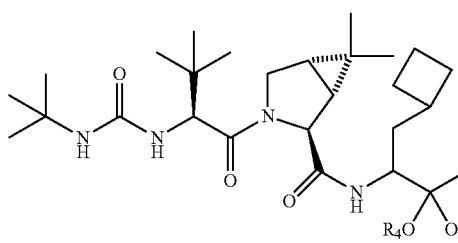
9b' vii) deprotecting/cleaving the acetal in the compound of Formula 9a or 9b' in the presence of an acid thereby obtaining telaprevir of Formula 1 or boceprevir according to Formula 25, or a pharmaceutically acceptable salt or solvate thereof.

2. Process for the preparation of a compound of Formula 7a

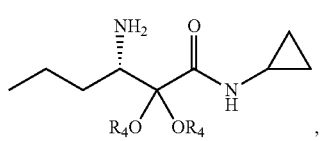
7a wherein $R_4$ is methyl or ethyl; comprising the steps of:
i) providing
(a) a compound of Formula 6a

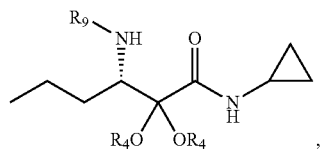
6a wherein $R_4$ is as defined above; and $R_9$ is a protective group; by applying the process steps (i)-(iv) of claim 1 and ii) deprotecting the compound of Formula 6a/6a' in order to provide
(a) a compound of Formula 7a, or
(b) a compound of Formula 7a'

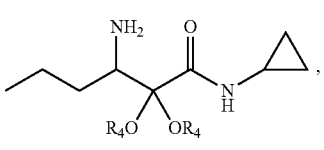
7a' and separating the racemic mixture 7a' to provide a compound of Formula 7a.

3. Process for the preparation of a compound of Formula 9a or 9b'

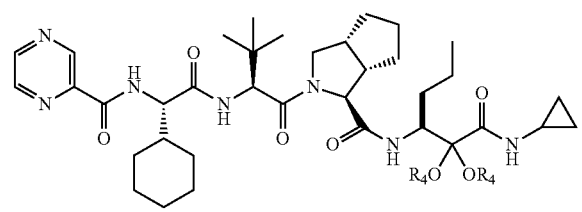
9a

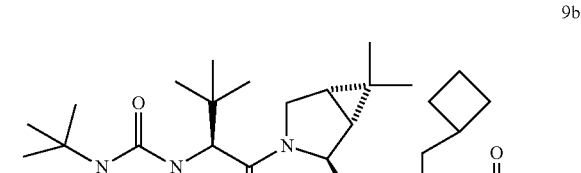
9b' wherein $R_4$ is methyl or ethyl; by applying the process steps (i) to (vi) as defined in claim 1.

* * * * *